(12) United States Patent
Warters et al.

(10) Patent No.: US 10,463,824 B2
(45) Date of Patent: Nov. 5, 2019

(54) VENTILATION DEVICES AND METHODS OF USE

(71) Applicant: MUSC FOUNDATION FOR RESEARCH DEVELOPMENT, Charleston, SC (US)

(72) Inventors: Robert D. Warters, Charleston, SC (US); Robert G. Dickie, King City (CA)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 430 days.

(21) Appl. No.: 14/351,355

(22) PCT Filed: Oct. 12, 2012

(86) PCT No.: PCT/US2012/060076
§ 371 (c)(1),
(2) Date: Apr. 11, 2014

(87) PCT Pub. No.: WO2013/056135
PCT Pub. Date: Apr. 18, 2013

(65) Prior Publication Data
US 2014/0230821 A1  Aug. 21, 2014

Related U.S. Application Data

(60) Provisional application No. 61/547,447, filed on Oct. 14, 2011, provisional application No. 61/547,823, filed on Oct. 17, 2011.

(51) Int. Cl.
*A61M 16/06* (2006.01)
*A61M 16/00* (2006.01)

(52) U.S. Cl.
CPC .... *A61M 16/0622* (2014.02); *A61M 16/0057* (2013.01)

(58) Field of Classification Search
CPC .... A61B 9/00; A61B 9/02–027; A61M 16/00; A61M 16/06–0694;
(Continued)

(56) References Cited

U.S. PATENT DOCUMENTS

| | | |
|---|---|---|
| 4,905,683 A | 3/1990 | Cronjaeger |
| 6,792,943 B2 | 9/2004 | Kumar et al. |

(Continued)

FOREIGN PATENT DOCUMENTS

| | | |
|---|---|---|
| CN | 2848246 | 12/2006 |
| CN | 201356886 | 12/2009 |

(Continued)

OTHER PUBLICATIONS

First Office Action and Search Report, dated Aug. 4, 2015, received in connection with Chinese Application No. 201280061681.1 (English Translation).

(Continued)

*Primary Examiner* — Tan-Uyen T Ho
*Assistant Examiner* — Ned T Heffner
(74) *Attorney, Agent, or Firm* — Meunier Carlin & Curfman LLC

(57) ABSTRACT

Provided are systems, devices and methods for ventilating patients. For example, provided are ventilation masks. The described ventilation masks can be used in ventilation procedures of patients.

11 Claims, 20 Drawing Sheets

(58) Field of Classification Search
CPC ... A61M 16/20–209; A61M 2016/0003–0042;
A61M 16/0057; A61M 16/0078; A61M
16/01; A61M 16/0616; A61M 16/0622;
A61M 16/0683; A61M 16/0833; A61M
16/085; A61M 2205/58; A61M 2205/586;
A61M 2210/0612; A61M 2210/0618;
A61M 2230/432; A61M 16/02–0205;
A62B 7/00; A62B 7/04; A62B 7/14;
A62B 18/00; A62B 18/10; B63C 11/12;
B63C 11/18; A61F 9/04
USPC ............ 128/203.16, 205.25, 206.21, 206.24,
128/206.25, 206.26, 206.28, 207.11,
128/207.13, 858; D24/110.1, 110.2,
D24/110.4
See application file for complete search history.

(56) References Cited

U.S. PATENT DOCUMENTS

| | | | |
|---|---|---|---|
| 6,966,317 B2 | 11/2005 | Bardel et al. | |
| 2003/0047189 A1* | 3/2003 | Kumar | A61M 16/06 128/206.29 |
| 2003/0127102 A1* | 7/2003 | Strawder | A61M 16/06 128/206.28 |
| 2003/0172932 A1* | 9/2003 | Matioc | A61M 16/06 128/206.24 |
| 2005/0098183 A1* | 5/2005 | Nash | A61M 16/06 128/206.21 |
| 2005/0121030 A1 | 6/2005 | Bateman et al. | |
| 2010/0089397 A1 | 4/2010 | Klockseth | |
| 2010/0122704 A1 | 5/2010 | Moenning | |
| 2011/0005524 A1 | 1/2011 | Veliss | |
| 2011/0132375 A1 | 6/2011 | Thornton | |

FOREIGN PATENT DOCUMENTS

| | | |
|---|---|---|
| JP | 2005021448 A | 1/2005 |
| JP | 2010022786 A | 2/2010 |

OTHER PUBLICATIONS

International Search Report and Written Opinion, dated Mar. 29, 2013, in connection with International Application No. PCT/US2012/060076.

Supplementary European Search Report, issued in European Application No. EP12839480, dated Feb. 16, 2015.

Chinese Office Action, dated Jan. 17, 2018, in connection with Chinese Application No. 201280061681.1.

* cited by examiner

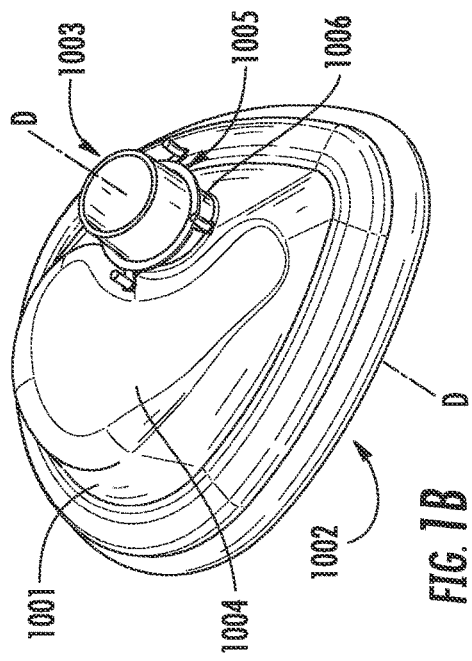
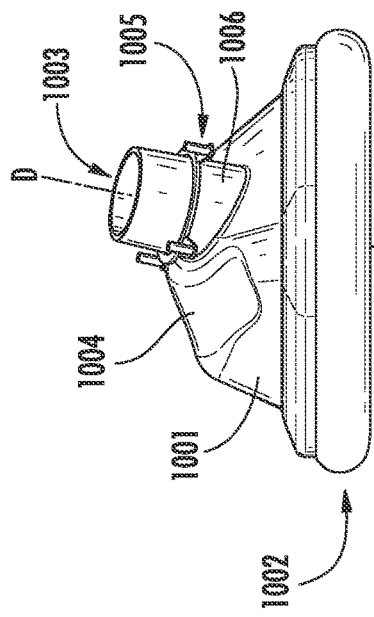
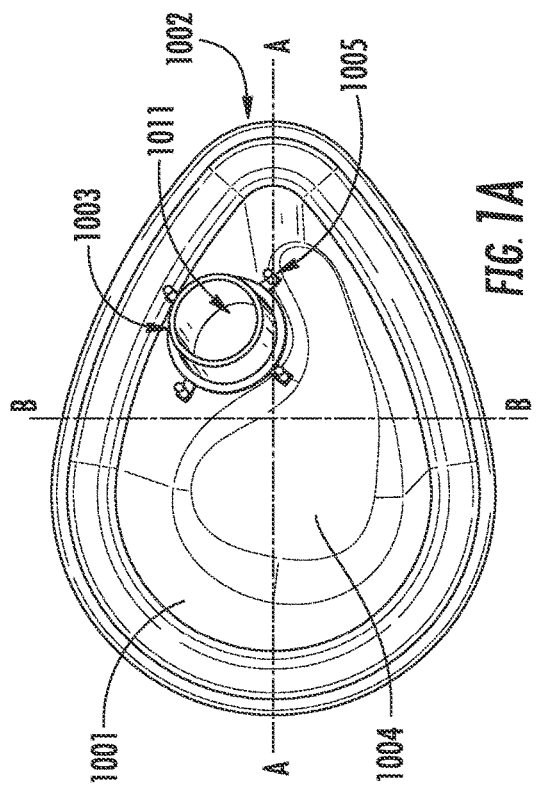
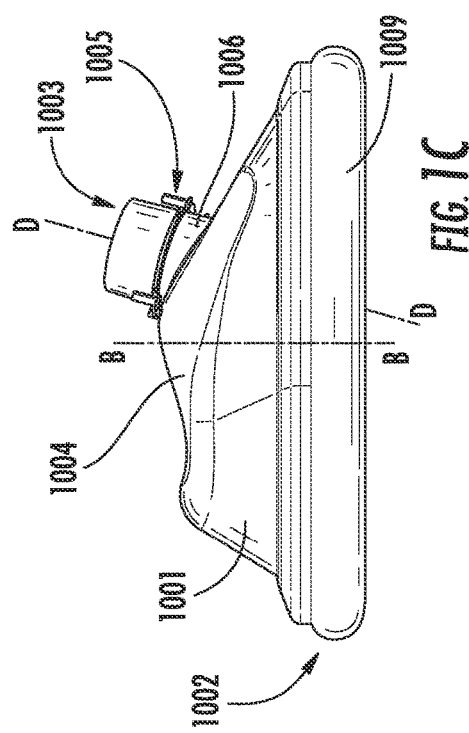
FIG. 1A
FIG. 1B
FIG. 1C
FIG. 1D

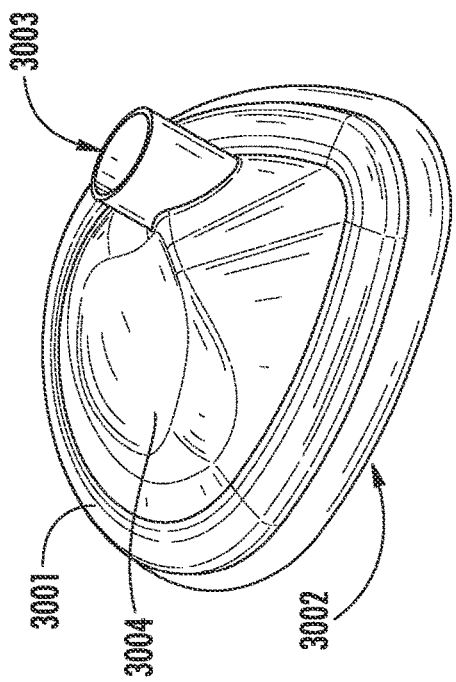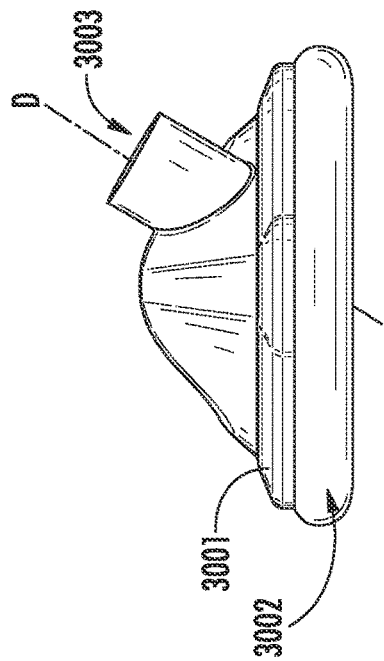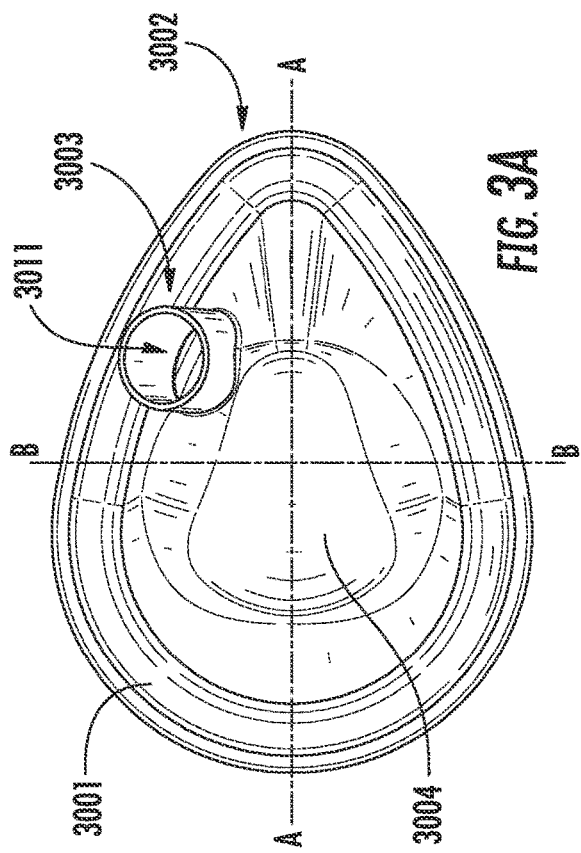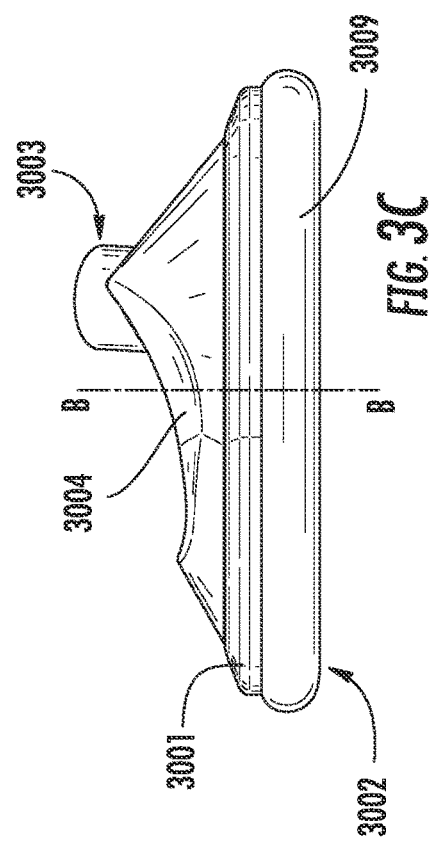

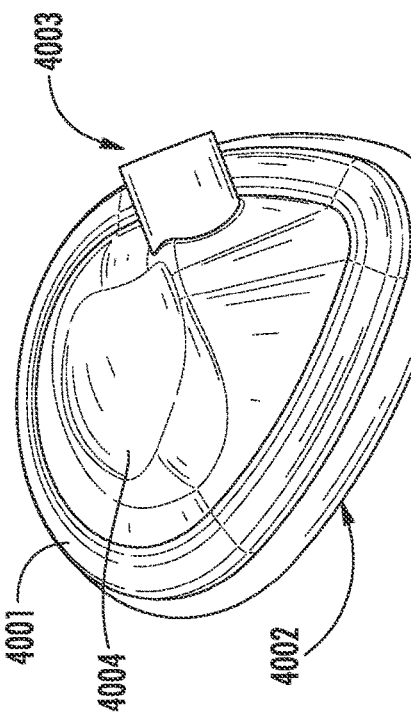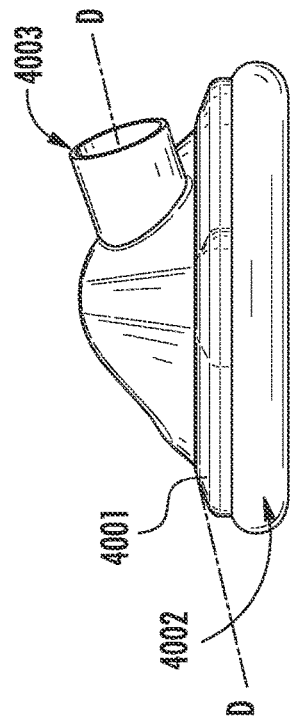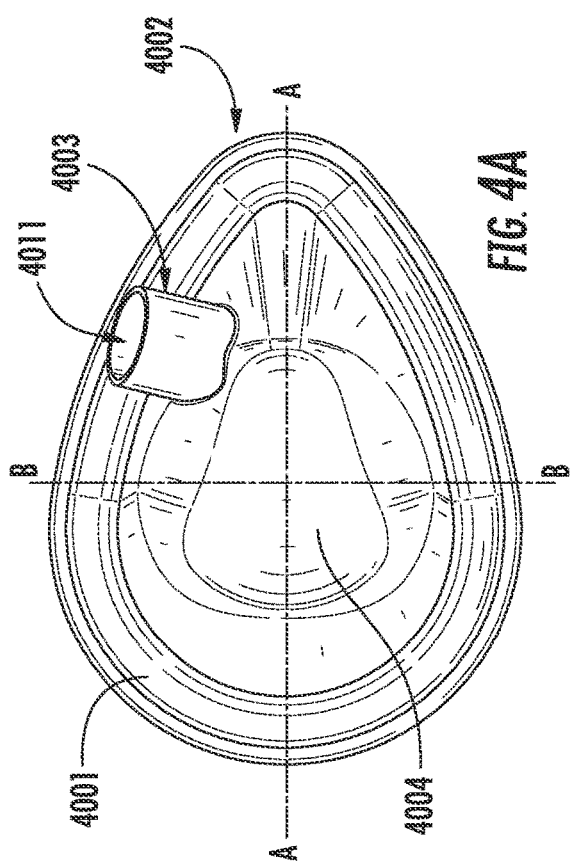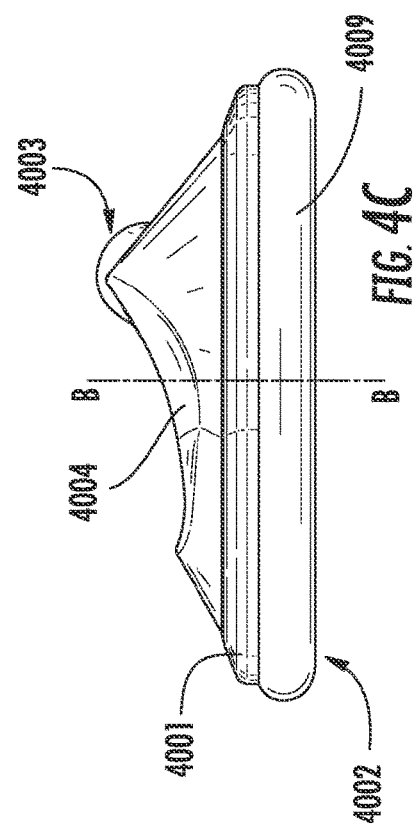

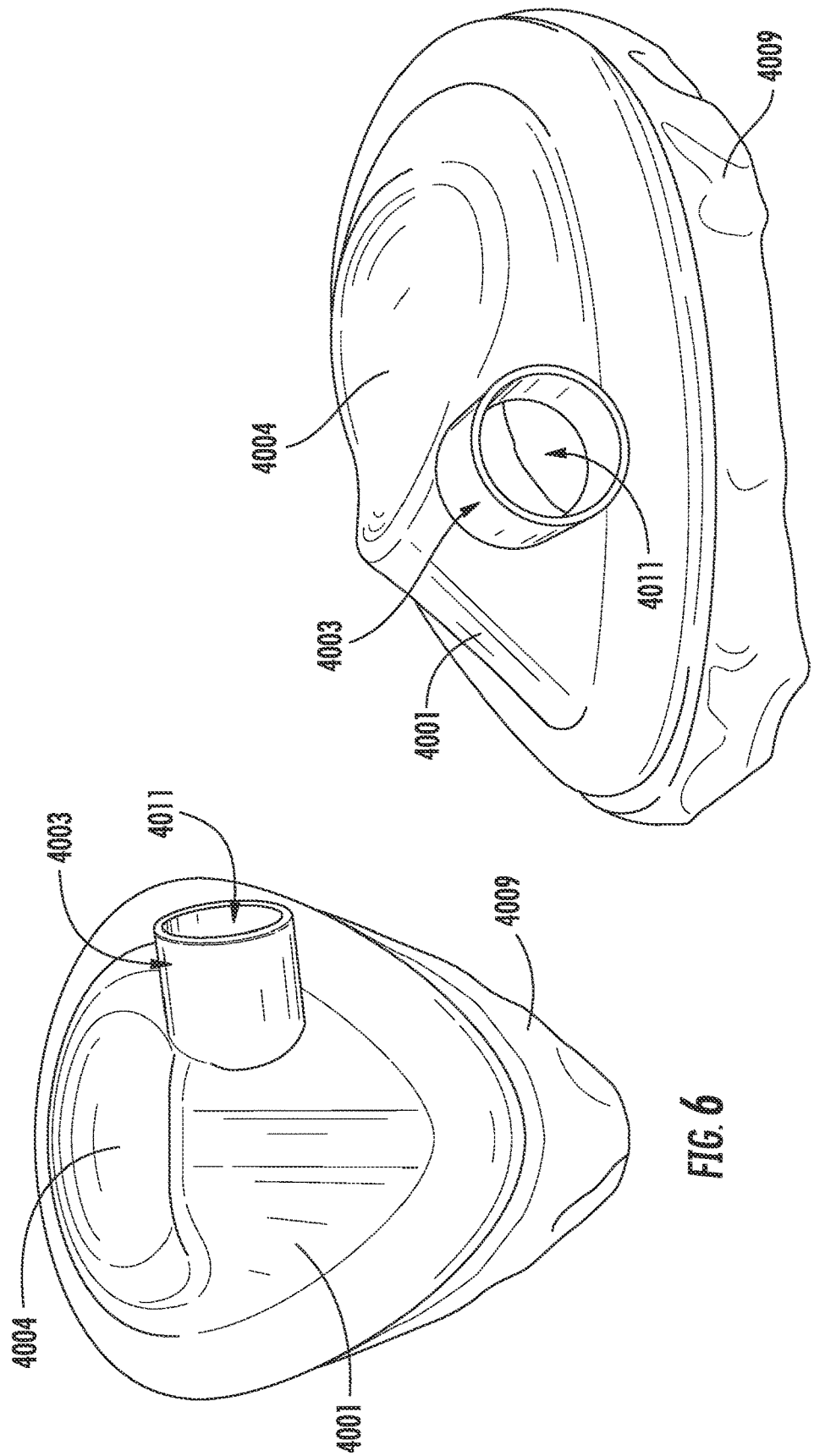

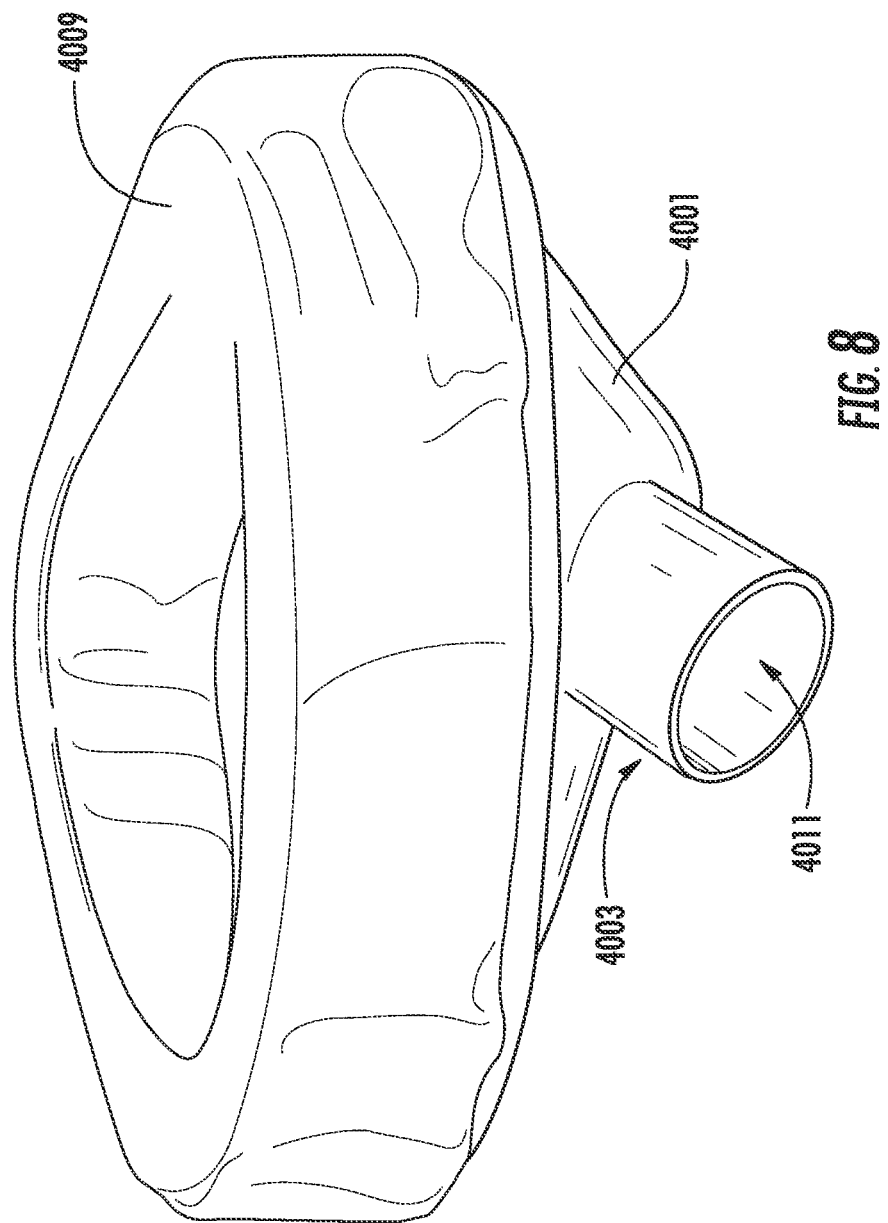

VENTILATION DEVICES AND METHODS OF USE

RELATED APPLICATIONS

This application claims the benefit of U.S. Provisional Application No. 61/547,447, filed Oct. 14, 2011, and U.S. Provisional Application No. 61/547,823, filed Oct. 17, 2011, both of which are herein incorporated by reference in their entireties.

TECHNICAL FIELD

This document relates to ventilation devices and to methods of using ventilation devices, for example to ventilate patients.

BACKGROUND

Face masks are routinely used to manually ventilate patients in conjunction with ambu bags as well as anesthesia machines. Conventional masks require the user to apply downward pressure with the thumb and index finger in order to seal the mask against the face while simultaneously lifting the jaw with the remaining fingers. This can be quite awkward due to the application of considerable pressure on the digits, which are stretched in unnatural angles, especially for users with diminutive hands.

SUMMARY

Provided are systems, devices and methods for ventilating patients. For example, provided are ventilation masks.

An example ventilation mask comprises a non-planar body sized to cover the nose and mouth of a patient, the ventilation mask having a mid-sagittal plane, a mid-frontal plane, and a peripheral patient contacting portion. The mask further comprises a neck that defines a passage through the body, the passage having a central mid-line axis. The central mid-line axis intersects the top surface of the mask at a mid-line intersection point. The top surface of the mask has a center point defined by the intersection of the top surface of the mask, the mid-sagittal plane, and the mid-frontal plane. The mid-line intersection point is offset from the center point.

The mid-line intersection point is optionally offset from the center point of the top surface of the face mask to an extent that allows placement of at least a portion of an operator's palm between the neck and the mid-sagittal plane of the face mask. The offset is optionally at least 3 neck diameters. The offset is optionally to the rear of the mid-frontal plane. The midline intersection point is optionally not offset from the mid-sagittal plane.

The peripheral patient contacting portion optionally comprises a sealing member. The sealing member is optionally configured to compress against the face of the subject to create an air-tight seal against the patient. The sealing member optionally comprises a deformable gas-filled bladder. The sealing member optionally comprises compressible foam. Optionally, the ventilation mask defines a mask-face volume when operatively positioned to cover the nose and mouth of the patient. The passage is optionally in communication with the mask-face volume when in operation.

The body optionally comprises an exterior surface having a contoured region. The contoured region is optionally at least partially concave. The concavity is optionally configured to accept at least a portion of the palm of an operator of the device. For example, the concavity is optionally configured to accept at least a portion of the left palm of the operator. Optionally, the ventilation mask is sized for ventilation of a pediatric patient.

The passage is optionally configured to be placed in communication with a source of gas or a ventilation device. For example, the ventilation device is optionally an ambu bag.

The passage is optionally located in the front right quadrant of the body.

The mid-frontal plane divides the mask into a front portion and a rear portion. Optionally, the mid-line intersection point is located in the front portion of the mask in front of the mid-frontal plane. Optionally, the neck has an outer surface and the outer surface does not intersect the mid-frontal plane. Optionally, the mid-line intersection point is located along the mid-sagittal plane. Optionally, the mid-line intersection point is located at a point along the mid-sagittal plane at a location that is spaced from the center point by a distance at least equal to the radius of the passage. For example, the mid-line intersection point is optionally located at a point along the mid-sagittal plane and is spaced from the center point by a distance of between 1 and 5 radii of the passage.

Further provided is a ventilation mask, comprising a body configured to operatively cover the nose and mouth of a patient to define a mask-face volume. The ventilation mask has a mid-sagittal plane and a neck that defines a passage through the body such that it operatively communicates with the mask-face volume and the passage has a central mid-line axis offset from the mid-sagittal plane of the ventilation mask.

Further provided is a ventilation mask comprising a non-planar body sized to cover the nose and mouth of a patient. The ventilation mask optionally has a mid-frontal plane and a peripheral patient contacting portion and a neck that defines a passage through the body. The passage has a central mid-line axis that is offset from the mid-frontal plane of the ventilation mask. The body further comprises a mid-sagittal plane, wherein the neck is optionally offset from the mid-sagittal plane.

Another example ventilation mask includes a face mask having a non-planar body sized to cover the nose and mouth of a patient. The face mask has a mid-sagittal plane and a peripheral patient contacting portion. A neck defines a passage through the body. The passage has a central mid-line axis that is offset from the mid-sagittal plane of the face mask.

Optionally, the peripheral patient contacting portion comprises a sealing member. The sealing member is configured to compress against the face of the subject to create an air-tight seal against the patient. For example, the sealing member optionally comprises a deformable gas-filled bladder. In another example, the sealing member optionally comprises compressible foam.

In operation, the face mask is configured to be seated on the face of a patient where it defines a mask-face volume when positioned to cover the nose and mouth of the patient. The passage is in communication with the mask-face volume when in operation.

Thus, the face mask body is configured to operatively cover the nose and mouth of a patient to define a mask-face volume. The neck defining the passage through the body operatively communicates with the mask-face volume.

Optionally, the body comprises an exterior surface having a contoured region. The contoured region is optionally at least partially concave. For example, the concavity is configured to accept at least a portion of the palm, optionally the left palm, of an operator of the device.

The neck is optionally positioned relative to the contoured region such that a portion of the palm of the operator is positionable on or in the contoured region while thumb and first forefinger of the operator are positionable on opposed regions of the neck. The passage is optionally located in the front right quadrant of the body.

The passage is configured to be placed in communication with a source of gas or a ventilation device. For example, the passage may be put in communication with an ambu bag.

Also provided are methods of ventilating a patient. The methods include covering the nose and mouth of the patient with a face mask. At least a portion of the palm of an operator's hand is placed onto the face mask. Each finger of the operator's hand, other than the thumb, can be placed under the chin of the patient. One or more of the fingers are used to pull the chin towards the mask and palm. Ventilating gas is then supplied to the subject through the mask. Optionally, the operator's left or right hand is used in each placing step.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic top-view illustration of an example ventilation mask.

FIG. 1B is a schematic perspective illustration of the example ventilation mask of FIG. 1A.

FIG. 1C is a schematic side-view illustration of the example ventilation mask of FIGS. 1A and 1B.

FIG. 1D is a schematic front-view illustration of the example ventilation mask of FIGS. 1A-1C.

FIG. 3A is a schematic top-view illustration of an example ventilation mask.

FIG. 3B is a schematic perspective illustration of the example ventilation mask of FIG. 3A.

FIG. 3C is a schematic side-view illustration of the example ventilation mask of FIGS. 3A and 3B.

FIG. 3D is a schematic front-view illustration of the example ventilation mask of FIGS. 3A-3C.

FIG. 4A is a schematic top-view illustration of an example ventilation mask.

FIG. 4B is a schematic perspective illustration of the example ventilation mask of FIG. 4A.

FIG. 4C is a schematic side-view illustration of the example ventilation mask of FIGS. 4A and 4B.

FIG. 4D is a schematic front-view illustration of the example ventilation mask of FIGS. 4A-4C.

FIG. 6 is a photograph showing a front view of an example ventilation mask.

FIG. 7 is a photograph showing a side view of an example ventilation mask.

FIG. 8 is a photograph showing a perspective bottom view of an example ventilation mask.

Like reference symbols in the various drawings indicate like elements.

DETAILED DESCRIPTION

Disclosed are medical devices for use in positive ventilation of patients. These devices incorporate improved ventilation face mask designs for ventilation of patients.

Face masks are used in anesthesia, emergency medicine and resuscitation as part of positive pressure mask ventilation, which allows the forceful, active administration of oxygen or anesthetic gasses from a source to a non-breathing patient. In the ventilation process, the face mask is the article through which oxygen or anesthetic gasses are administered to a patient.

When ventilating, the attending physician or emergency medical technician, uses a bag-mask device and holds the face mask over a patient's mouth and nose with the left hand while squeezing the bag (develops positive pressure air flow) with the right hand. There are many different mask designs. There are problems, however, associated with existing face mask designs.

In particular, existing masks are not well designed for single-hand clamping of the mask over the face of the patient. State of the art ventilation of a patient by a medical personnel, or even a by-stander, requires that the person administrating the oxygen place the patient on their back and stand at the patient's head. In this configuration, the person administering the oxygen then places the mask on the patient and grips the mask against the patient's face with their left hand.

With a single hand the administrator must place fingers under the patient's chin, in a claw-like position, pulling back against the chin while pushing down on the mask with the palm and forefinger and thumb of the same hand to keep the seal of the mask against the face.

Figure 5:
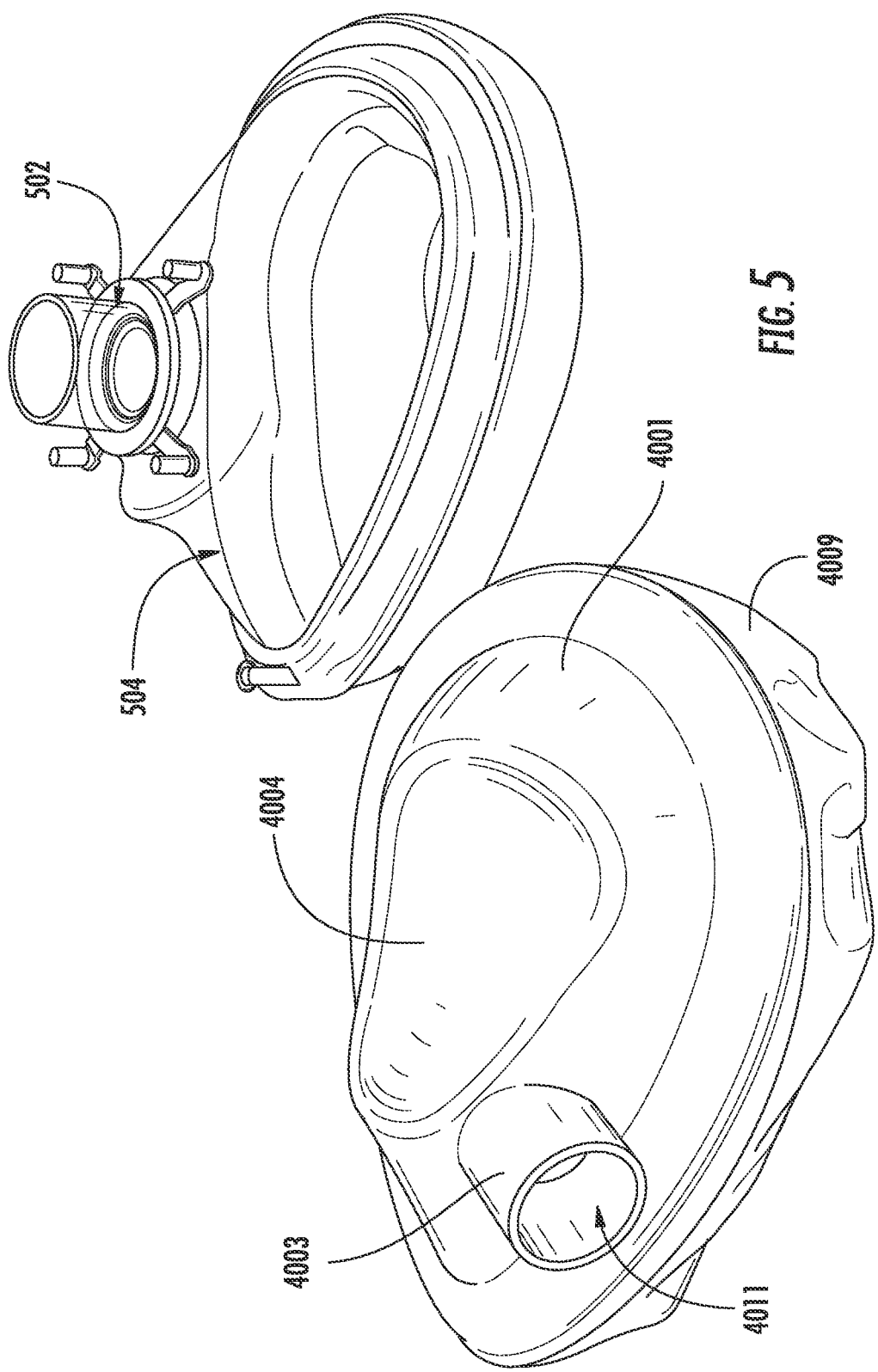
FIG. 5 is a photograph showing a perspective view of a face mask with a centered neck, and a perspective view of a showing an example ventilation mask.

Because of the central position of the neck 502, as shown in FIG. 5, connecting the tube from the oxygen or anesthesia producing device while sealing the mask over the patient's nose and mouth causes significant contortions in the hand of the individual administering the ventilation.

Existing mask designs inhibit constant and successful positive pressure mask ventilation. The quality of the seal between the mask and the face can be affected by the patient's facial bone structure, facial hair or other factors. Maintaining this seal is critical and often requires increased pressure applied to the face. Maintaining the correct claw-like grip required with a central neck 502 is uncomfortable, tiring, and painful especially when increased force is necessary to obtain and maintain a seal, as is the case with certain facial hair and bone structures.

The disclosed face masks provide solutions to the strained grip requirements of the existing designs, as well as providing ergonomic benefits. The disclosed face masks move the neck off of center, or the center top region, while, optionally, at the same time, altering the shape of the face mask body to more accurately achieve hand placement while performing the preferred claw-like grip. The disclosed devices can also have the same form factor as conventional face masks, and can be fully compatible with existing systems.

The disclosed masks optionally have the neck for ventilation bag connection moved out of the center region of the mask. The center region of the mask is defined as the region of the mask at the top surface of the mask, from a point defined by the mid-sagittal plane intersecting with the mid-frontal plane at the topmost surface of the mask, and extending from this point in a circle defined by a radius which is 25% of the width of the mask from left to right in the sagittal plane of the mask. In certain embodiments the area of the center region can be reduced to a radius of 10%, 15%, or 20% of the width of the mask from the left to the right in the sagittal plane of the mask.

Also disclosed are masks where the point of intersection of the longitudinal axis of the passage created by the neck (such as in FIG. 1, neck 1003 and passage 1011, with axis D-D) and the top surface of the mask is offset, in any direction, from the point created at the top surface of the mask created by the mid-frontal plane and the mid-sagittal plane intersection by, or at least, or more than 0.25 neck diameters, 0.5 neck diameters, 0.75 neck diameters, 1 neck diameter, 1.5 neck diameters, 2 neck diameters, 2.5 neck diameters, 3 neck diameters, 3.5 neck diameters, 4 neck diameters, 4.5 neck diameters, 5 neck diameters, 5.5 neck diameters, 6 neck diameters, 6.5 neck diameters, 7 neck diameters, 8 neck diameters, 8.5 neck diameters, 9 neck diameters, 9.5 neck diameters, or 10 neck diameters.

Also disclosed are masks where the point of intersection of the longitudinal axis of the passage created by the neck (such as in FIG. 1, neck 1003 and passage 1011, with axis D-D) and the top surface of the mask is offset, in any direction, from the point created at the top surface of the mask created by the bisection of the mid-frontal plane and the mid-sagittal plane, in the direction of the quadrant defined by the rear side of the mid-frontal plane and the right side of the mid-sagittal plane, by the rear side of the mid-frontal plane and the left side of the mid-sagittal plane, by the front side of the mid-frontal plane and the right side of the mid-sagittal plane, or by the front side of the mid-frontal plane and the left side of the mid-sagittal plane, where for example, the neck is offset in the amounts disclosed herein.

Also disclosed are masks where the point of intersection of the longitudinal axis of the passage created by the neck (such as in FIG. 1, neck 1003 and passage 1011, with axis D-D) and the top surface of the mask is offset, in any direction, from the point created at the top surface of the mask created by the bisection of the mid-frontal plane and the mid-sagittal plane, in the direction of the rear side of the mid-frontal plane, the front side of the mid-frontal plane, the right side of the mid-sagittal plane, or the left side of the mid-sagittal plane, where for example, the neck is offset in the amounts disclosed herein.

Also disclosed are masks where the point of intersection of the longitudinal axis of the passage created by the neck (such as in FIG. 1, neck 1003 and passage 1011, with axis D-D) and the top surface of the mask remains on the line created by the intersection of the mid-sagittal plane with the top surface of the mask, but is offset from the point created at the top surface of the mask created by the bisection of the mid-frontal plane and the mid-sagittal plane, where for example, the neck is offset in the amounts disclosed herein.

FIGS. 1-14 show example ventilation face masks. The disclosed face masks are designed to optionally attach to air bags, such as an ambu bag, which is squeezed by a medical personal to ventilate a patient. Previous designs, an example of which is shown in FIG. 5, utilize a neck to connect the ventilation bag or device where the neck is centered in the mask. Because of the need to grip the mask and the patient's face with the left hand, so that the ambu bag or ventilation device can be squeezed to displace air with their right hand, unless the mask is held tightly to the face, the air displaced from the bag will not be forced into the lungs, but rather will escape through the non-tight seal between the mask and the face of the patient.

When the neck is in the center of the mask, it requires a claw-like grip where some of the fingers of the left hand wrap under the chin from the side of the mask and the thumb and forefinger extend over the top of the mask to compress in squeezing motion, the mask to the face. This not only is uncomfortable, but also results in imperfect ventilation of a patient at times, particularly under stressed or emergency type situations. It can also result in cramping of the hand placing further risk on the patient and the medical personnel.

The disclosed face masks allow medical personnel to take a more centered grip where all of the fingers can drape over the back end (chin) of the mask and naturally continue down under the chin where they can pull up on the chin against the mask which is pushing back against the palm. In this position, the user of the device can naturally, with little effort, compress the mask down on the face by lightly pulling up against the chin with the fingers. Because of the off center position of the neck (for example, offset from the center region or center point of the top surface as described herein), the hand rests palm side against the non-face side of the mask with the neck optionally falling in the "V"-shaped area between the forefinger and the thumb. Positioning the neck in the V-shaped position is optionally used in applications where the mask is of a size that allows the user to drape the fingers over the back end of the chin while locating the neck between a forefinger and thumb of the operator. Such applications optionally involve small sized masks. For example, the neck is optionally positioned in the V-shaped area for ventilation of pediatric patients using pediatric sized ventilation masks. Optionally, the neck can be positioned to the front of the mask, towards where the mask contacts the bridge or surrounding area of the patients nose.

Optionally, the disclosed face masks are configured to fit with an airtight seal between the mask and the face. This seal occurs in a continuous line, for example, starting at the bridge of the nose, and then moving laterally underneath the right eye and down the face, and beginning to turn under the mouth and then when reaching the left side of the mouth, heading up toward the left eye, and the finally going back up over the left side of the nose, connecting at again at the bridge.

The masks are optionally able to be compressed on the face to form an air tight seal, while not compressing the face surface of the mask against the nose. The masks cover both the nose and the mouth. When compressed against the face, the masks create a mask-face volume, within which, air can be ventilated. Optionally, the masks can comfortably fit on the cheeks of the patient, rather than up on the nose. Optionally, a compact face mask is provided which reduces the mask-face volume, and which optionally utilizes such a position.

The disclosed masks can be made in different sizes. For example, different sizes are optionally used to fit different sized patients. For example, the mask can be made in a size to ventilate a baby, including premature babies, or very large masks for overweight patients.

The masks can be made out of any suitable material. For example, the masks can be made from polypropylene, or any other plastic, as well as foam, and even glass.

FIGS. 1A-1D are schematic illustrations of an example ventilation mask. The example ventilation mask includes a face mask having a non-planar body 1001 sized to cover the nose and mouth of a patient. A non-planar body is a body that is not flat such that when portions of the body are placed against a surface, or in plane with a surface, other portions of the body are elevated above the surface.

The disclosed masks, including those shown in FIGS. 1-14, have three planes. For purposes of the masks disclosed herein, the back or rear of the mask is considered the portion of the mask designed to go near the mouth, the front of the mask is the portion designed to go near the nose, the side of the mask near as the mask is placed on the face of a patient under the right eye is the right side of the mask, and the side of the mask under the left eye is the left side of the mask, and lastly the side of the mask that is designed to touch the face is the bottom side of the mask and the side not touching the face is the top side of the mask.

With this understanding, the masks have sagittal planes, dividing the mask between left and right, transverse planes dividing the mask into top and bottom, and frontal planes dividing the mask into front and back. Midway between left and right on the masks, there is a mid-sagittal plane. Midway between the top and bottom of the masks there is a mid-transverse plane. Midway between the front and back of the masks there is a mid-frontal plane. It is understood that all of the planes also have an axis, the mid-sagittal axis, the mid-transverse axis, and the mid-frontal axis, which is the line within the plane midway between the boundaries defining the plane.

Figure 9A:
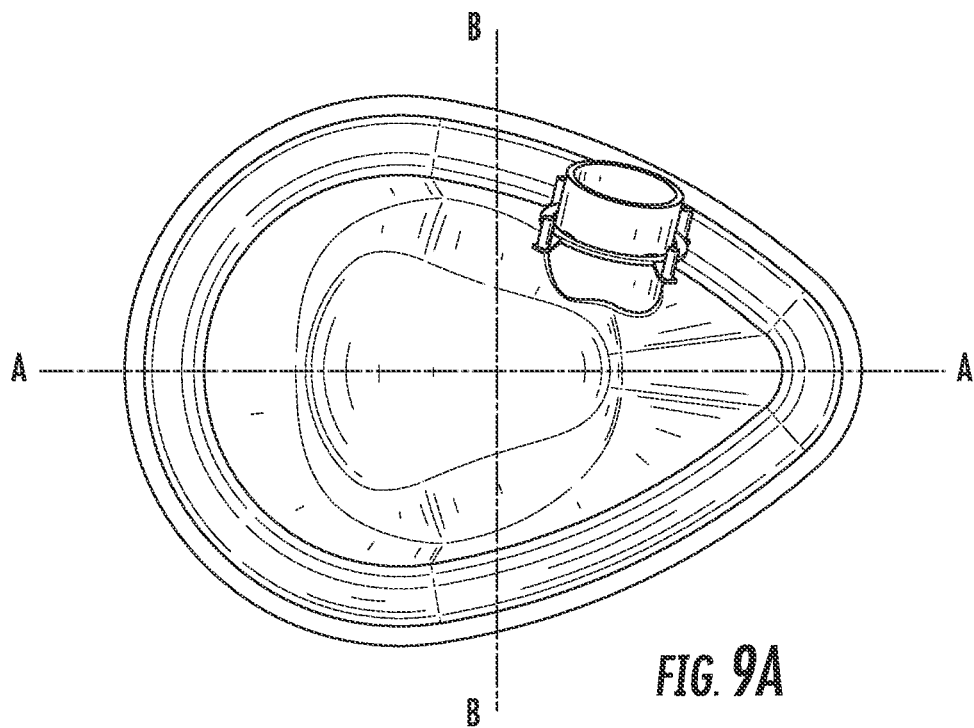
FIG. 9A is a schematic top view illustration of an example face mask with a mid-sagittal axis A-A.
Figure 9B:
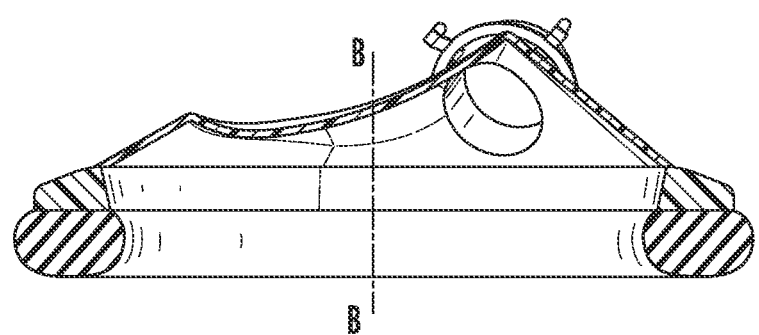
FIG. 9B is a schematic section view illustration of the right half of the mask of FIG. 9A taken across the mid-sagittal plane including the mid-sagittal axis A-A.

FIG. 9A is a top view schematic illustration of a face mask with a mid-sagittal plane A-A and a mid-fontal plane B-B. FIG. 9A also illustrates the central mid-line axis of the passage neck, which is labeled D-D in FIG. 9G. The central mid-line axis D-D of the passage neck is offset from the mid-sagittal plane A-A of the mask. FIG. 9B is a schematic section view that illustrates the right half of the mask taken across the mid-sagittal plane including the mid-sagittal plane A-A, and also shows the mid-frontal plane B-B.

Figure 9C:
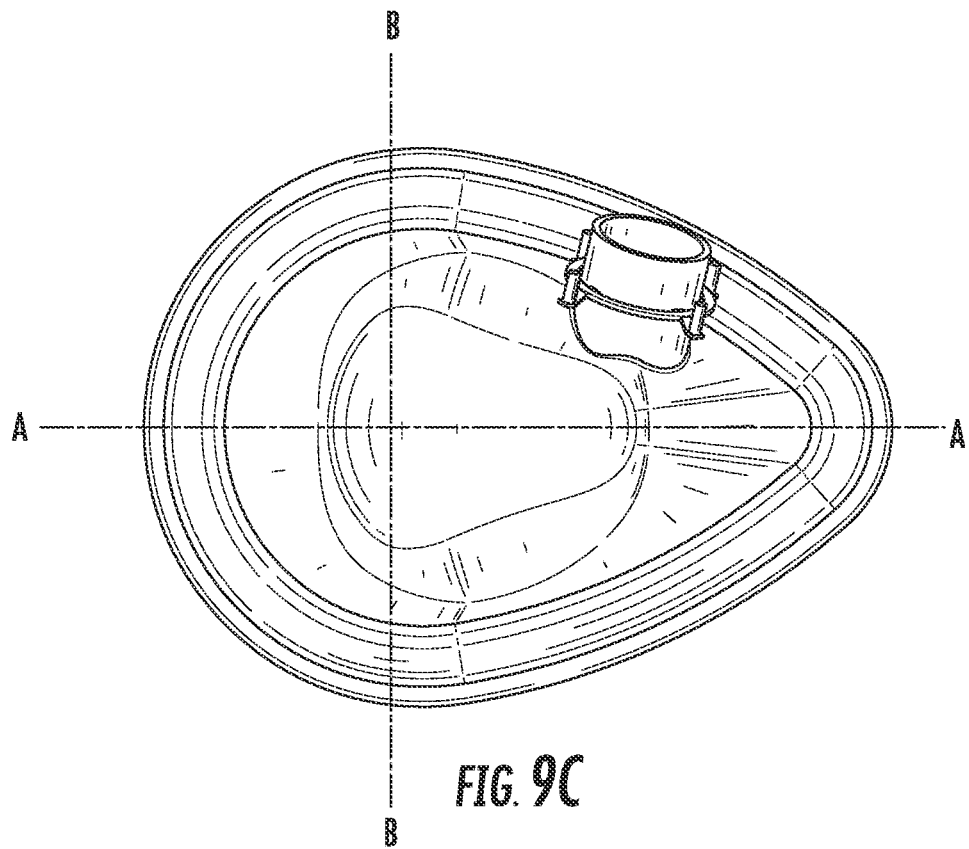
FIG. 9C is a schematic top view illustration of the facemask of FIG. 9A with a frontal axis B-B that divides the mask into a front, that includes the neck, and a back, without a neck.
Figure 9D:
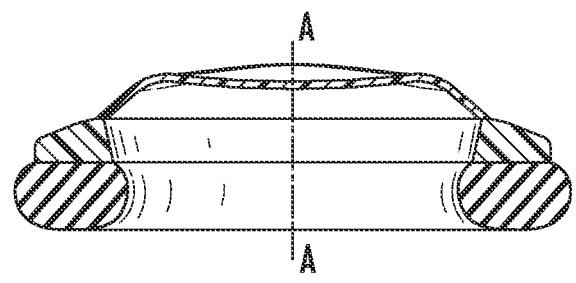
FIG. 9D is a schematic section view illustration of the back half of the mask taken across the frontal plane B-B shown in FIG. 9C.

FIG. 9C is a top view schematic illustration of a face mask with a plane B-B that divides the mask into a front, that includes the neck, and a back or rear, without a neck. FIG. 9C also illustrates the central mid-line axis of the passage neck, which is offset from the mid-sagittal plane of the mask. FIG. 9D is a schematic section view that illustrates the back half of the mask taken across the frontal plane B-B, as well as the mid-sagittal plane A-A.

Figure 9E:
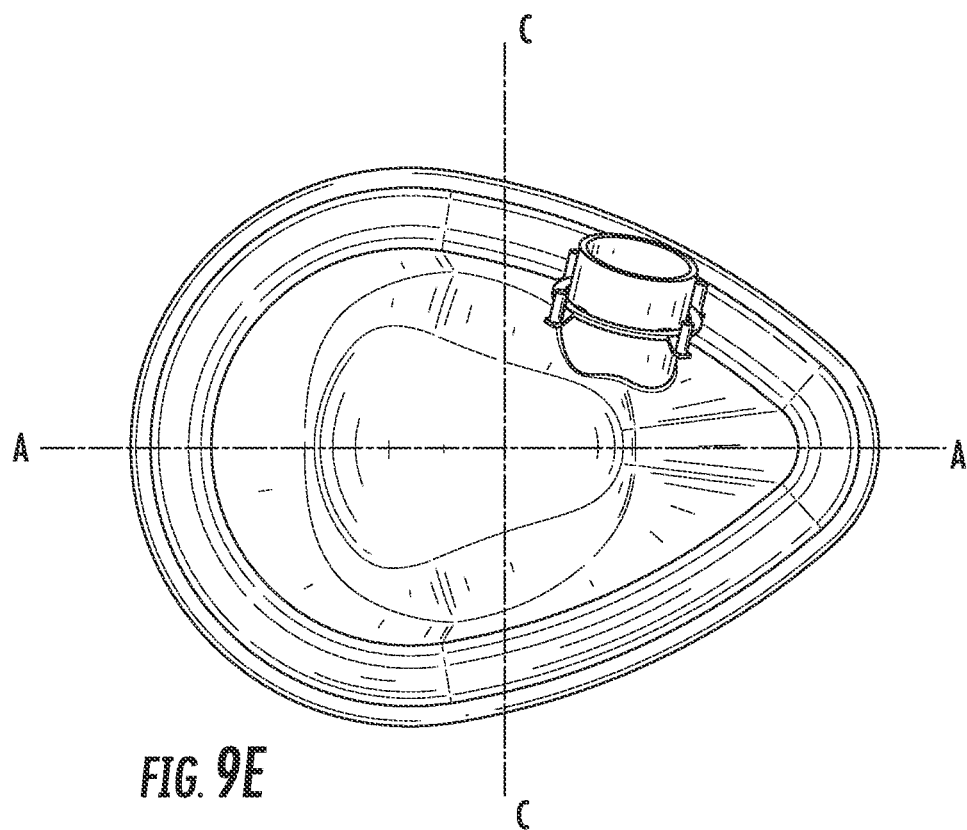
FIG. 9E is a schematic top view illustration of the face mask of FIG. 9A with a mid-frontal axis C-C that divides the mask into a front, with the neck and a back, without a neck.
Figure 9F:
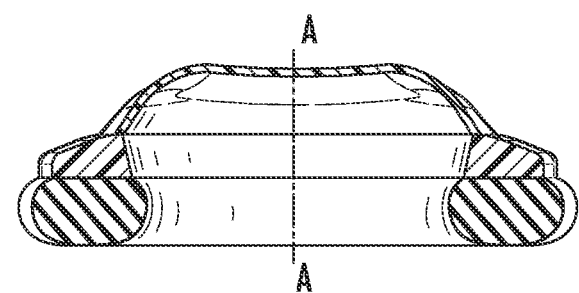
FIG. 9F is a schematic section view that illustrates the back half of the mask taken across the mid-frontal plane C-C shown in FIG. 9E.
Figure 9G:
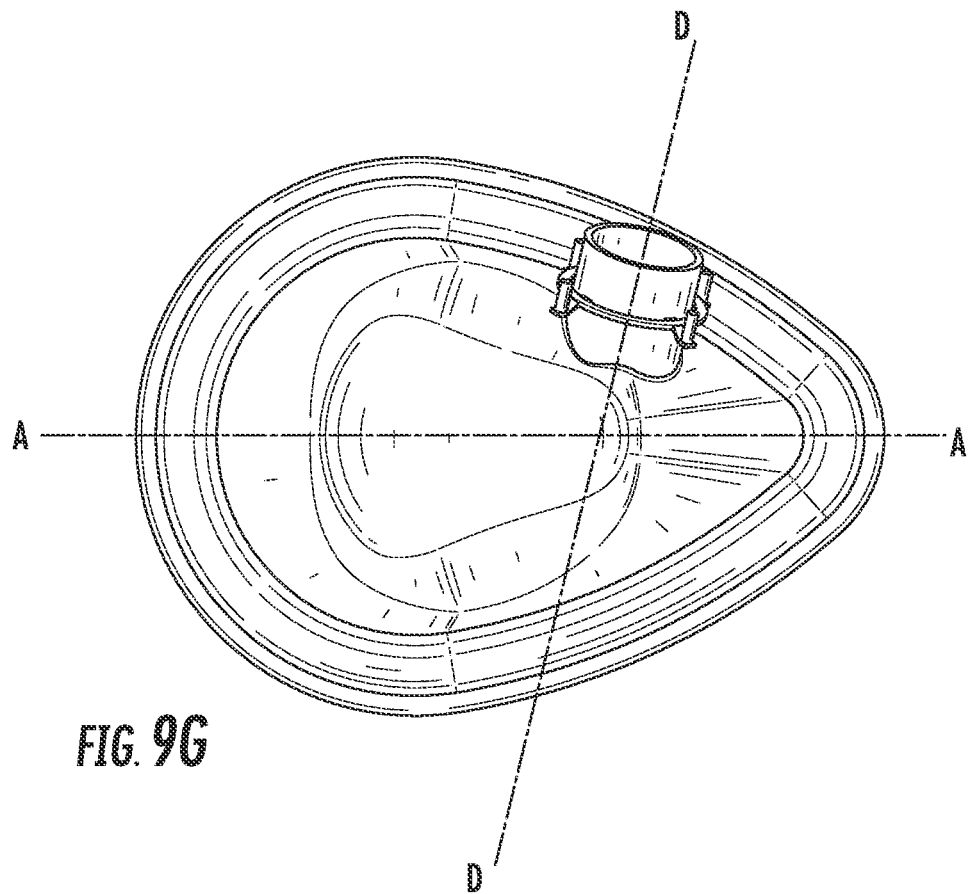
FIG. 9G is schematic illustration of the mask of FIG. 9A showing the central mid-line axis D-D of a passage of the neck.
Figure 9H:
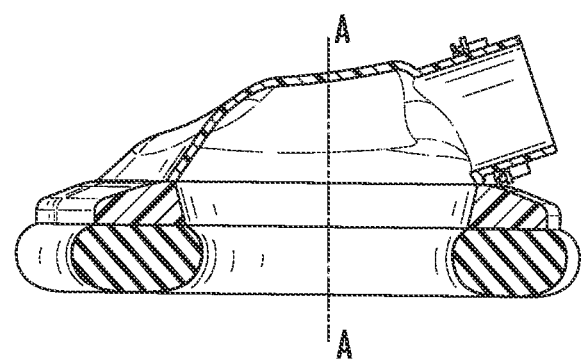
FIG. 9H is a schematic section view of the mask taken across the central mid-line axis D-D shown in FIG. 9G, across the frontal plane, looking to the back of the mask.

FIG. 9E is a top view schematic illustration of a face mask with a mid-frontal plane C-C that divides the mask into a front, with the neck and a back, without a neck, as well as the mid-sagittal plane A-A. FIG. 9E also illustrates the central mid-line axis of the passage neck, which is offset from the mid-sagittal plane of the mask. FIG. 9F is a schematic section view that illustrates the rear or back half of the mask taken across the mid-frontal plane C-C.

Referring again to FIGS. 1A-D, the face mask has a mid-sagittal plane A-A and a peripheral patient contacting portion 1002. A neck 1003 defines a passage 1011 through the body 1001. The passage 1011 has a central mid-line axis D-D. The central mid-line axis is offset from the mid-sagittal plane of the face mask.

The peripheral patient contacting portion 1002 optionally comprises a sealing member 1009. The sealing member 1009 is configured to compress against the face of the subject to create an air-tight seal against the patient when the face mask is used.

The sealing member 1009 can be made from any material that can form a seal with skin, such as a gas filled bladder having the ability to be compressed when pressure is placed on the bladder causing a distension, which can cause a seal. For example, the sealing member 1009 optionally comprises a deformable gas-filled bladder. Optionally, the sealing member comprises compressible foam, as illustrated in FIGS. 5, 6, 7 and 8. The sealing member can also be made from a compressible rubber. The sealing member 1009 is optionally connected to or is an integral part of the body 1001 of the face mask.

The body 1001 of the face mask is designed such that it can accommodate a sealed volume over the face comprising the nose and mouth of a patient. The shape and the volume of this space optionally allows air to be exchanged in the volume through the neck 1003 of the face mask unimpeded by parts of the face while also not making consistent contact with the face other than through the seal. The mask optionally contacts the bridge of the nose, above a part on the nose which will compress the nostrils such that there is not free airflow into or out of the nose.

The neck 1003 is placed off-center of the face mask. By off-center it means the central midline axis D-D of the passage 1011 is displaced from the mid-sagittal plane A-A of the body. This can be contrasted with the central configuration used in the prior art, and as shown in FIG. 5, where the central midline axis of the neck 502 is positioned over the mid-sagittal plane of the body 504.

The neck 1003 can be any size or diameter. Optionally, the neck 1003 has a diameter and connectivity capable of hooking to standard connection equipment used for ventilation such as hand compressed air bags, such as an ambu bag. In addition to being any size or any diameter, the neck 1003 can also be any shape. Thus, the cylindrical shape shown in the neck 1003 is optional. Other example shapes would include oval, triangular, and even square shapes, as well as non uniform shapes further designed to approximate the approximate V delineation created by the thumb and forefinger of the human hand.

In most cases, all of these shapes will include a definite $3^{rd}$ dimension away from the body of the face mask, such as the height dimension shown in the cylindrical neck 1003 of FIGS. 1A-D. It is also understood that these shapes and the volume created by the neck need not be uniform or symmetrical. For example, the neck may be wider at the base (where it flows into or is attached to the body) than at the distal end, where attachment to another device will take place. In addition the neck can be different shapes at different transverse planes of the neck. For example, the neck can be cylindrical at the distal end, where attachment to devices takes place, and more oval shaped at the base in an increasing flaring width, such that the base of the neck attempts to contour with the placement of the thumb and forefinger when gripping the mask.

The neck placement is optionally such that the axial center line, or central midline axis D-D of the neck is at least, no more, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent from the mid-sagittal plane A-A of the face mask body 1001 to the edge of the face mask, defined by the seal member 1009 on a line perpendicular from the axial midline, through the central midline axis D-D of the neck, to the edge of the face mask.

Optionally, the axial midline D-D of the neck 1003 is placed perpendicular to the face mask but this is not required. The neck 1003 can also have bends and turns in it designed to either accommodate non-perpendicular positions, or desired or different placement for connection to ventilation equipment.

The neck 1003 is optionally positioned in the front right quadrant of the mask as defined when the mask is operatively placed on a patient. This configuration is shown in FIG. 1A. Thus, the front right quadrant of the mask would be the quadrant of the mask nearest the right eye of the patient when the mask is placed on the patient, defined by the right side of the mid-sagittal plane and the front side of the mid-frontal plane. This placement provides a reduced relationship for the optional positioning of the neck in the "V"-shape formed between the forefinger and thumb of the left hand of the medical personnel when placing their hand on the mask to compress it against the face of the patient. However, the neck is optionally positioned in the V-shape for ventilation of pediatric patients using pediatric sized ventilation masks.

Optionally, the central mid-line axis is offset from the mid-sagittal axis of the face mask to an extent that allows placement of at least a portion of an operator's palm between the neck and the mid-sagittal axis of the face mask. The placement of at least a portion of the palm between the neck and the central mid-sagittal axis of the face mask allows an operator to apply inward pressure to the center area of the mask with the portion of the palm that is so positioned.

The mask also optionally comprises a contoured region 1004. The contoured region 1004 is optionally configured to receive at least a portion the palm of the left hand of the medical personnel. The contoured region 1004 does not have to have perfect contact with all parts of all palms of medical personnel, but rather can optionally include curved depressions available for the part of the palm extending from the base of the thumb can be cradled as the thumb and forefinger are naturally placed with the neck 1003 in the "V"-space between the thumb and forefinger, or such that the thumb is naturally cradled between the neck and forefinger of the clinician's hand.

The face mask can also have various attachment devices, as well as connectors, or adaptors, such as 1005 and 1006. Theses connectors can facilitate attachment to ventilating devices such for connection to an ambu bag. Under certain circumstances the neck, either because of size, or shape, or position, for example, is connected to the ventilation device, through one or more adaptors, such as 1005 and 1006. These adaptors can have standard parts and shapes to them. Typically, they are designed to match up with and connect the face mask via the neck to standard ventilation equipment.

FIGS. 2A-2D are schematic illustrations of another example ventilation mask. Similar to the ventilation mask shown in FIGS. 1A-1D, the example ventilation mask shown in FIGS. 2A-2D includes a face mask having a non-planar body 2001 sized to cover the nose and mouth of a patient. The face mask has a mid-sagittal plane A-A and a peripheral patient contacting portion 2002. A neck 2003 defines a passage 2011 through the body 2001. The passage 2011 has a central mid-line axis D-D. The central mid-line axis is offset from the mid-sagittal plane of the face mask.

The peripheral patient contacting portion 2002 optionally comprises a sealing member 2009. The sealing member 2009 is configured to compress against the face of the subject to create an air-tight seal against the patient when the face mask is used.

As described above, the sealing member 2009 can be made from any material that can form a seal with skin, such as a gas filled bladder having the ability to be compressed when pressure is placed on the bladder causing a distension, which can cause a seal. For example, the sealing member 2009 optionally comprises a deformable gas-filled bladder. Optionally, the sealing member comprises compressible foam, as illustrated in FIGS. 5, 6, 7 and 8. The sealing member can also be made from a compressible rubber. The sealing member 2009 is optionally connected to or is an integral part of the body 2001 of the face mask.

The body 2001 of the face mask is designed such that it can accommodate a sealed volume over the face comprising the nose and mouth of a patient. The shape and the volume of this space optionally allows air to be exchanged in the volume through the neck 2003 of the face mask unimpeded by parts of the face while also not making consistent contact with the face other than through the seal. The mask optionally contacts the bridge of the nose, above a part on the nose which will compress the nostrils such that there is not free airflow into or out of the nose.

The neck 2003 is placed off-center of the face mask. By off-center it means the central midline axis D-D of the passage 2011 is displaced from the mid-sagittal plane A-A of the body. This can be contrasted with the central configuration shown in FIG. 5 where the central midline axis of the neck 502 is positioned over the mid-sagittal plane of the body 504.

The neck 2003 can be any size or diameter. Optionally, the neck 2003 has a diameter and connectivity capable of hooking to standard connection equipment used for ventilation such as hand compressed air bags, such as an ambu bag.

The neck placement is optionally such that the axial center line, or central midline axis D-D of the neck is at least, no more, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent from the mid-sagittal axis A-A of the face mask body 2001 to the edge of the face mask, defined by the seal member 2009 on a line perpendicular from the axial midline, through the central midline axis D-D of the neck, to the edge of the face mask.

The neck 2003 can have bends and turns in it designed to either accommodate non-perpendicular positions, or desired or different placement for connection to ventilation equipment. The central midline axis neck D-D, for example as shown in FIGS. 2A-2D, may be at an angle other than perpendicular to the mid-sagittal plane.

Figure 2B:
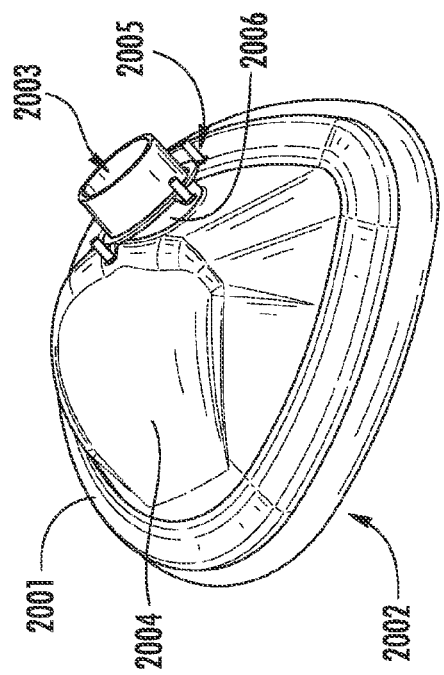
FIG. 2B is a schematic perspective illustration of the example ventilation mask of FIG. 2A.
Figure 2D:
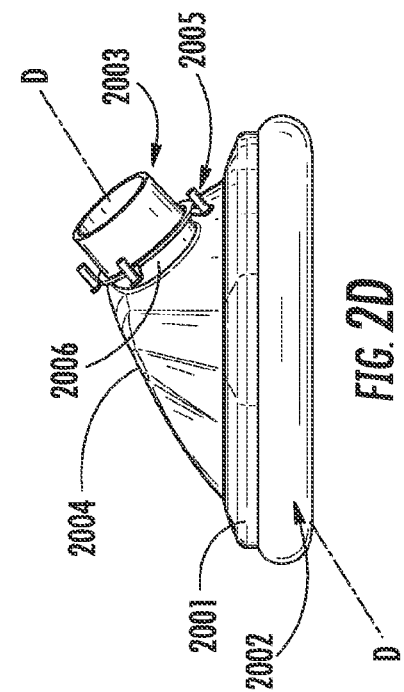
FIG. 2D is a schematic front-view illustration of the example ventilation mask of FIGS. 2A-2C.
Figure 2A:
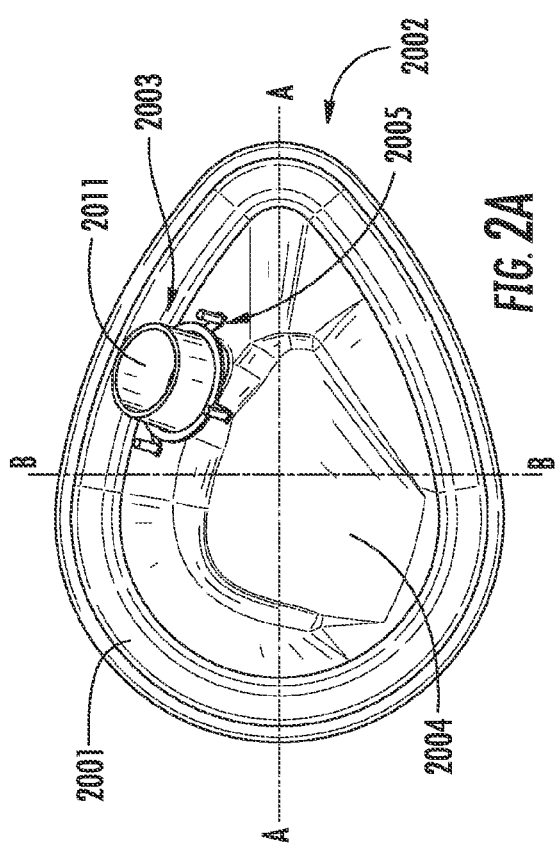
FIG. 2A is a schematic top-view illustration of an example ventilation mask.
Figure 2C:
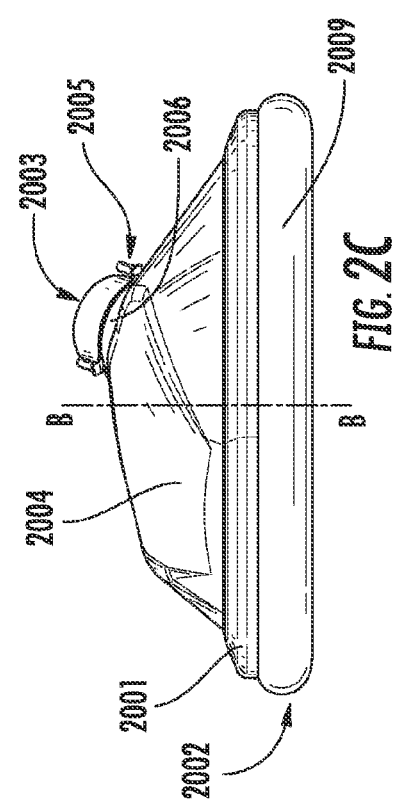
FIG. 2C is a schematic side-view illustration of the example ventilation mask of FIGS. 2A and 2B.

The neck 2003 is optionally positioned in the front right quadrant of the mask as defined when the mask is operatively placed on a patient. This configuration is shown in FIG. 2A. Thus, the front right quadrant of the mask would be the quadrant of the mask nearest the right eye of the patient when the mask is placed on the patient, defined by the right side of the mid-sagittal plane and the front side of the mid-frontal plane. This placement provides a good relationship for the optional positioning of the neck in the "V"-shape formed between the forefinger and thumb of the left hand of the medical personnel when placing their hand on the mask to compress it against the face of the patient. For example, the neck is optionally positioned in the V-shape for ventilation of pediatric patients using pediatric sized ventilation masks.

The mask also optionally comprises a contoured region 2004. The contoured region 2004 is optionally configured to receive at least a portion the palm of the left hand of the medical personnel. The contoured region 2004 does not have to have perfect contact with all parts of all palms of medical personnel, but rather can optionally include curved depressions available for the part of the palm extending from the base of the thumb can be cradled as the thumb and forefinger are naturally placed with the neck 2003 in the "V"-space between the thumb and forefinger, or such that the thumb is naturally cradled between the neck and the forefinger of the clinician's hand.

The face mask can also have various attachment devices, as well as connectors, or adaptors, such as 2005 and 2006. Theses connectors can facilitate attachment to ventilating devices such for connection to an ambu bag.

FIGS. 3A-3D are schematic illustrations of another example ventilation mask. Similar to the ventilation masks illustrated in FIGS. 1A-1D and 2A-2D, the example ventilation mask includes a face mask having a non-planar body 3001 sized to cover the nose and mouth of a patient. The face mask has a mid-sagittal plane A-A and a peripheral patient contacting portion 3002. A neck 3003 defines a passage 3011 through the body 3001. The passage 3011 has a central mid-line axis D-D. The central mid-line axis is offset from the mid-sagittal plane of the face mask.

The peripheral patient contacting portion 3002 optionally comprises a sealing member 3009. The sealing member 3009 is configured to compress against the face of the subject to create an air-tight seal against the patient when the face mask is used.

The sealing member 3009 can be made from any material that can form a seal with skin, such as a gas filled bladder having the ability to be compressed when pressure is placed on the bladder causing a distension, which can cause a seal. For example, the sealing member 3009 optionally comprises a deformable gas-filled bladder. Optionally, the sealing member comprises compressible foam, as illustrated in FIGS. 5, 6, 7 and 8. The sealing member can also be made from a compressible rubber. The sealing member 3009 is optionally connected to or is an integral part of the body 3001 of the face mask.

The body 3001 of the face mask is designed such that it can accommodate a sealed volume over the face comprising the nose and mouth of a patient. The shape and the volume of this space optionally allows air to be exchanged in the volume through the neck 3003 of the face mask unimpeded by parts of the face while also not making consistent contact with the face other than through the seal. The mask optionally contacts the bridge of the nose, above a part on the nose which will compress the nostrils such that there is not free airflow into or out of the nose.

The neck 3003 is placed off-center of the face mask. By off-center it means the central midline axis D-D of the passage 3011 is displaced from the mid-sagittal plane A-A of the body. This can be contrasted with the central configuration shown in FIG. 5 where the central midline axis of the neck 502 is positioned over the mid-sagittal plane of the body 504.

The neck 3003 can be any size or diameter. Optionally, the neck 3003 has a diameter and connectivity capable of hooking to standard connection equipment used for ventilation such as hand compressed air bags, such as an ambu bag.

The neck placement is optionally such that the axial center line, or central midline axis D-D of the neck is at least, no more, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent from the mid-sagittal axis A-A of the face mask body 3001 to the edge of the face mask, defined by the seal member 3009 on a line perpendicular from the axial midline, through the central midline axis D-D of the neck, to the edge of the face mask.

The neck 3003 can have bends and turns in it designed to either accommodate non-perpendicular positions, or desired or different placement for connection to ventilation equipment. The central midline axis neck D-D, for example as shown in FIGS. 3A-3D, may be at angle other than perpendicular to the mid-sagittal plane.

The neck 3003 is optionally positioned in the front right quadrant of the mask as defined when the mask is operatively placed on a patient. This configuration is shown in FIG. 3A. Thus, the front right quadrant of the mask would be the quadrant of the mask nearest the right eye of the patient when the mask is placed on the patient, defined by the right side of the mid-sagittal plane and the top side of the mid-transverse plane. This placement provides a good relationship for the optional positioning of the neck in the "V"-shape formed between the forefinger and thumb of the left hand of the medical personnel when placing their hand on the mask to compress it against the face of the patient. For example, the neck is optionally positioned in the V-shape for ventilation of pediatric patients using pediatric sized ventilation masks.

The mask also optionally comprises a contoured region 3004. The contoured region 3004 is optionally configured to receive at least a portion the palm of the left hand of the medical personnel. The contoured region 3004 does not have to have perfect contact with all parts of all palms of medical personnel, but rather can optionally include curved depressions available for the part of the palm extending from the base of the thumb can be cradled as the thumb and forefinger are naturally placed with the neck 3003 optionally in the "V"-space between the thumb and forefinger, or such that the thumb is naturally cradled between the neck and the forefinger of the clinician's hand.

The face mask can also have various attachment devices, as well as connectors, such as 3005 and 3006. Theses connectors can facilitate attachment to ventilating devices such for connection to an ambu bag.

FIGS. 4A-4D are schematic illustrations of an example ventilation mask. Similar to the ventilation masks shown in FIGS. 1A-1D, 2A-2D and 3A-3D, the example ventilation mask includes a face mask having a non-planar body 4001 sized to cover the nose and mouth of a patient. The face mask has a mid-sagittal plane A-A and a peripheral patient contacting portion 4002. A neck 4003 defines a passage 4011 through the body 4001. The passage 4011 has a central mid-line axis D-D. The central mid-line axis is offset from the mid-sagittal plane of the face mask.

The peripheral patient contacting portion 4002 optionally comprises a sealing member 4009. The sealing member 4009 is configured to compress against the face of the subject to create an air-tight seal against the patient when the face mask is used.

The sealing member 4009 can be made from any material that can form a seal with skin, such as a gas filled bladder having the ability to be compressed when pressure is placed on the bladder causing a distension, which can cause a seal. For example, the sealing member 4009 optionally comprises a deformable gas-filled bladder. Optionally, the sealing member comprises compressible foam, as illustrated in FIGS. 5, 6, 7 and 8. The sealing member can also be made from a compressible rubber. The sealing member 4009 is optionally connected to or is an integral part of the body 4001 of the face mask.

The body 4001 of the face mask is designed such that it can accommodate a sealed volume over the face comprising the nose and mouth of a patient. The shape and the volume of this space optionally allows air to be exchanged in the volume through the neck 4003 of the face mask unimpeded by parts of the face while also not making consistent contact with the face other than through the seal. The mask optionally contacts the bridge of the nose, above a part on the nose which will compress the nostrils such that there is not free airflow into or out of the nose.

The neck 4003 is placed off-center of the face mask. By off-center it means the central midline axis D-D of the passage 4011 is displaced from the mid-sagittal plane A-A of the body. This can be contrasted with the central configuration shown in FIG. 5 where the central midline axis of the neck 502 is positioned over the mid-sagittal plane of the body 504.

The neck 4003 can be any size or diameter. Optionally, the neck 4003 has a diameter and connectivity capable of hooking to standard connection equipment used for ventilation such as hand compressed air bags, such as an ambu bag.

The neck placement is optionally such that the axial center line, or central midline axis D-D of the neck is at least, no more, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent from the mid-sagittal plane A-A of the face mask body 4001 to the edge of the face mask, defined by the seal member 4009 on a line perpendicular from the axial midline, through the central midline axis D-D of the neck, to the edge of the face mask.

The neck 4003 can have bends and turns in it designed to either accommodate non-perpendicular positions, or desired or different placement for connection to ventilation equipment. The central midline axis neck D-D, for example as shown in FIGS. 4A-4D, may be at any angle other than coextensive with to the mid-sagittal plane.

The neck 4003 is optionally positioned in the front right quadrant of the mask as defined when the mask is operatively placed on a patient. This configuration is shown in FIG. 4A. Thus, the front right quadrant of the mask would be the quadrant of the mask nearest the right eye of the patient when the mask is placed on the patient, defined by the right side of the mid-sagittal plane and the front side of the mid-frontal plane. This placement provides a reduced relationship for the optional positioning of the neck in the "V"-shape formed between the forefinger and thumb of the left hand of the medical personnel when placing their hand on the mask to compress it against the face of the patient. However, the neck is optionally positioned in the V-shape for ventilation of pediatric patients using pediatric sized ventilation masks.

The mask also optionally comprises a contoured region 4004. The contoured region 4004 is optionally configured to receive at least a portion the palm of the left hand of the medical personnel. The contoured region 4004 does not have to have perfect contact with all parts of all palms of medical personnel, but rather can optionally include curved depressions available for the part of the palm extending from the base of the thumb can be cradled as the thumb and forefinger are naturally placed with the neck 4003 in the "V"-space between the thumb and forefinger or such that the thumb is naturally cradled between the neck and the forefinger of the clinician's hand.

The face mask can also have various attachment devices, as well as connectors, such as 4005 and 4006. Theses connectors can facilitate attachment to ventilating devices such for connection to an ambu bag.

FIG. 5 is a perspective view of a face mask with a centered neck, which represents the prior art, and an example ventilation mask as illustrated schematically in FIGS. 4A-4D. In the example ventilation mask shown in FIG. 5, the sealing member comprises compressible foam. FIG. 6 is a photograph showing a front view of the ventilation mask of FIGS. 4A-4D and FIG. 5. FIG. 7 is a photograph showing a side view of the same example ventilation mask. FIG. 8 is a photograph showing a perspective bottom view of the example ventilation mask.

FIGS. 10A-J show various views of an embodiment where the neck location on the face mask does not interfere with the palm of the operators hand, in the front half of the face mask, but is in the line of mold draw, for example, on the mid-sagittal plane, and in certain embodiments, down the mid-sagittal axis in the front half of the mask. The neck, when being placed on the mid-sagittal plane, may also be anywhere on the mid-transverse plane, including on the mid-transverse axis, and in certain embodiments, the neck may be on the mid-sagittal/mid-transverse axis of the mask.

In certain embodiments, the neck does not obscure the rim, a junction between the body 1001 of the face mask and a sealing member 1009, when the face mask is constructed from at least two separate parts, such as when there are at least two injection molding cycles for each part, so the secondary injection cycle to join the mask body to the sealing member will function as other mask molding designs.

In certain embodiments a manufacturer of the disclosed masks can use existing sealing members and existing secondary injection tooling with the disclosed body 1001 of the face mask.

In certain embodiments, the neck coming out of the body of the face mask can be vertical, which provides certain desirable characteristics for attachment to the air bag, such as with ball valve masks that utilize a 90 degree angle to the inlet neck on the mask body for connection of the bag to the face mask.

In certain embodiments, the mask can have a collar (FIGS. 10A and B, 10001) that locates the strap (such as elastic) pins closer to the center of the mask.

Figure 10A:
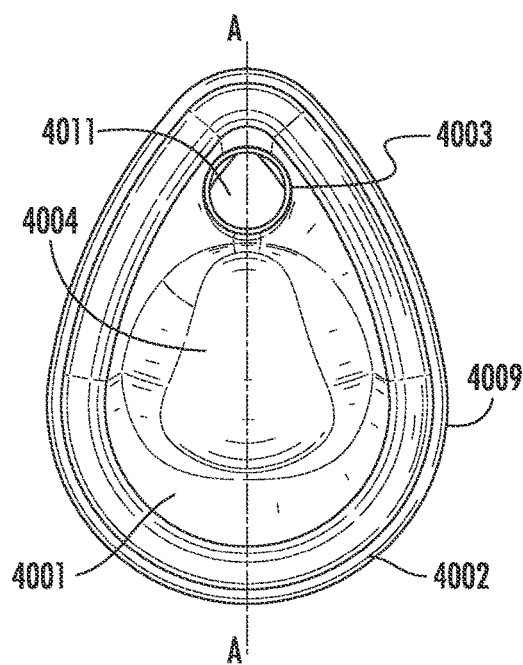
FIGS. 10A-J are schematic illustrations showing a variety of views of a mask having the neck on the mid-sagittal axis in the rear portion of the mask, such that the neck will not interfere with the clinician's hand when placing his palm on the mask as described herein.
Figure 10B:
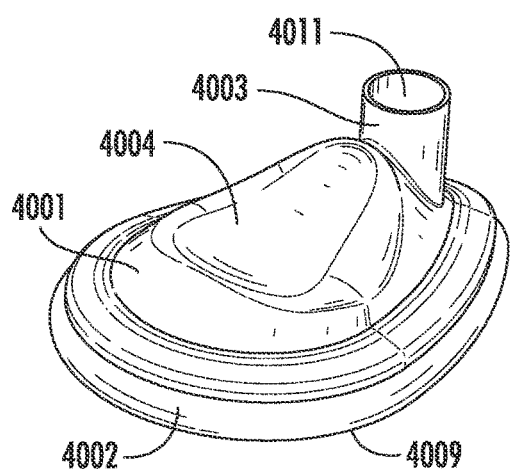
Figure 10C:
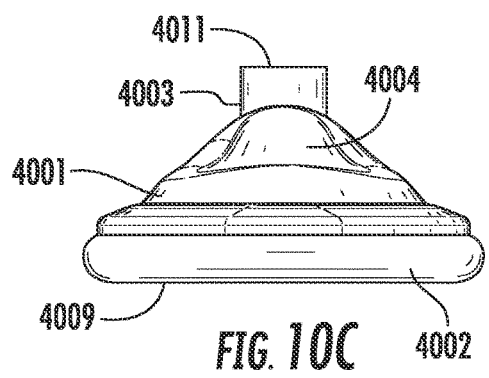
Figure 10D:
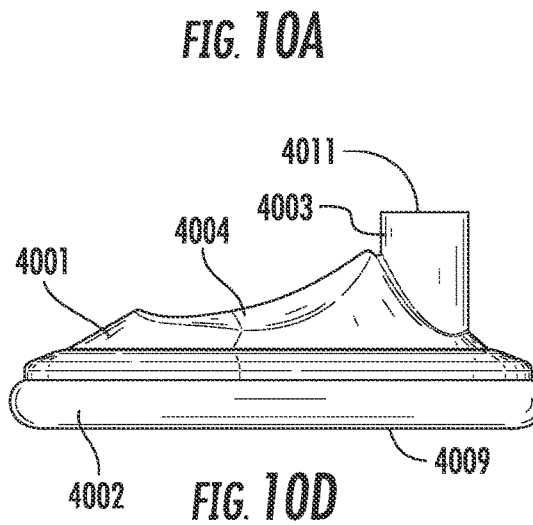
Figure 10E:
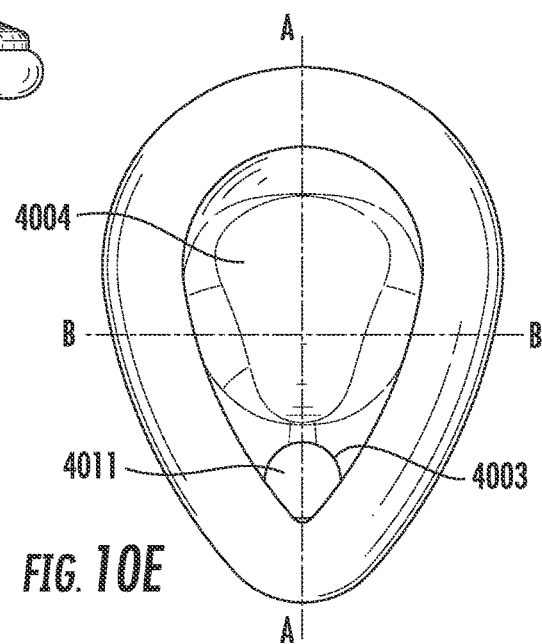
Figure 10F:
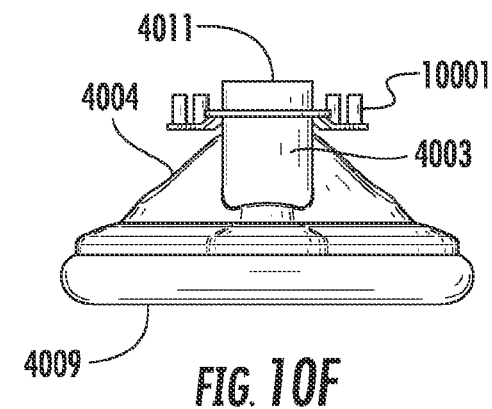
Figure 10G:
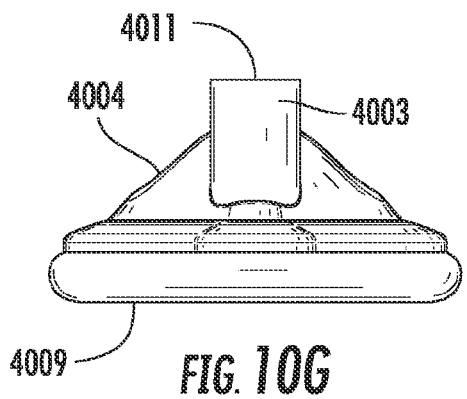
Figure 10H:
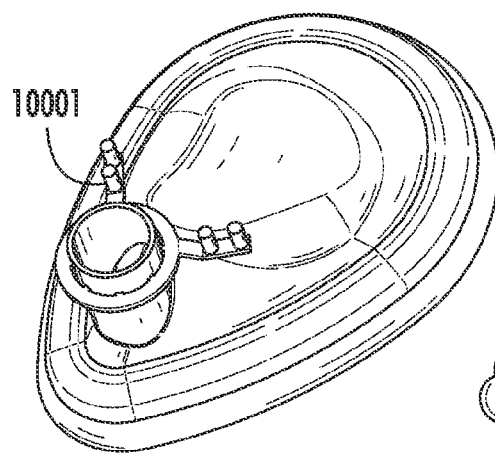
Figure 10I:
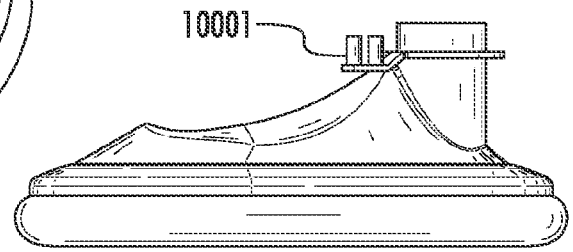
Figure 10J:
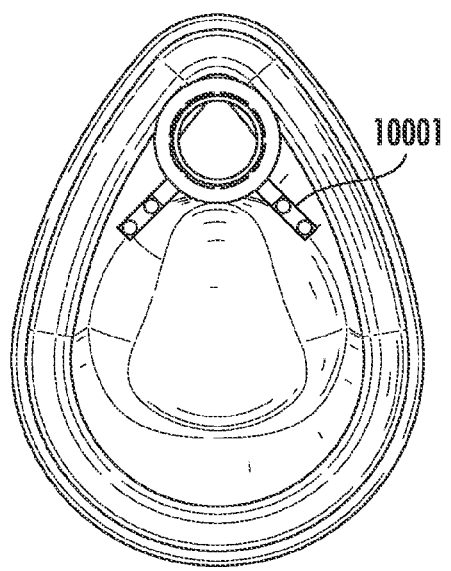
Figure 11:
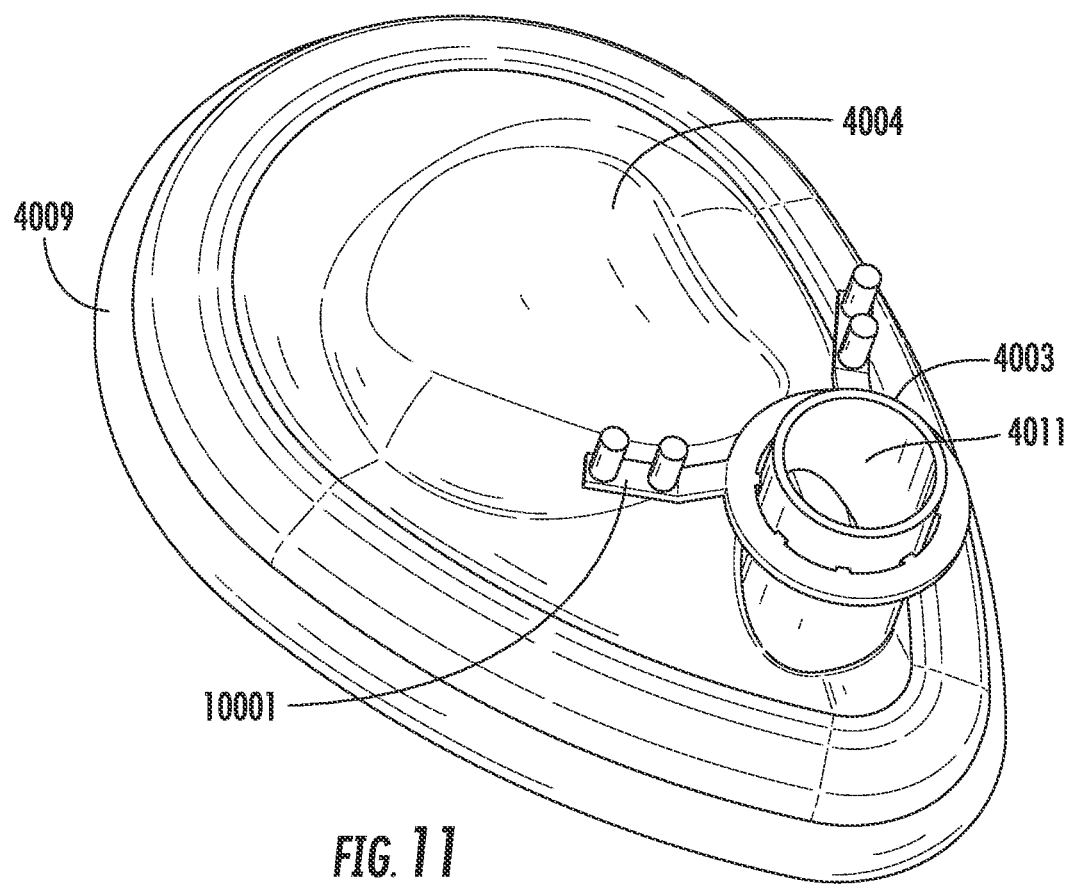
FIG. 11 is a perspective illustration of an embodiment of the face mask disclosed having the neck on the mid-sagittal axis in the rear portion of the mask, such that the neck will not interfere with the clinician's hand when placing his palm on the mask as described herein.

In certain embodiments, there is a front facing neck, such as in FIGS. 10A and B. In these embodiments, the neck can be moved toward the front or back of the mask along the mid-sagittal plane and towards the top or the bottom of the mask along the mid-transverse plane to minimize interference with a clinician's hand. Furthermore, the connecting surface of the face mask interacting with the neck can be angled in a variety of ways to alter the position of the neck as desired. The angle of the surface of the face mask interacting with the neck in the region over the nose is limited typically by not being in or minimizing contact with the nose of the patient.

In certain embodiments, the top of the mask can be raised to have more interior clearance for big nosed patients. The top can be raised incrementally.

In certain embodiments, the height of the contour ridge 4003, the ridge defining the transition of the contoured palm region of the mask, can be raised to provide a better grasp on the mask in certain situations. The contour ridge can be raised incrementally.

In certain embodiments, the mask can comprise a strap system, such as an elastic, strap system, for strapping the mask onto the patient. In certain embodiments, this strap system can be positioned to minimize interference with the grip of the mask, but remain functional.

In certain embodiments, the neck can be found on the side of the mask or towards the front of the mask, including on the mid-sagittal axis and/or the mid-transverse axis in the front section of the mask. In certain embodiments, these necks can be bent or straight.

In certain embodiments, the contoured region where the palm rests can be increased to a convex configuration.

When using the mask, in certain uses the clinician can be seated to the right side of the patient when the patient is laying on his or her back. In this position, often the right side of the head is generally facing the chest of the clinician, the left hand/arm is naturally angled such that a neck centered on the mid-sagittal axis (such as a mid-sagittal plane neck at the rear of the mask, FIG. 10, for example). As is clear, the neck provides no or minimal obstruction to the operator from placing their palm on the mask, in this overall usage configuration. As masks get smaller, in this configuration and usage, the clinician may have to adjust positioning depending on the operator's hand and preferred angle.

In certain embodiments, the face masks can be produced using a side core in the mold, if the molding direction and the neck are not in alignment. Alternatively, embodiments disclosed herein can have the neck in alignment with the molding direction.

Figure 12A:
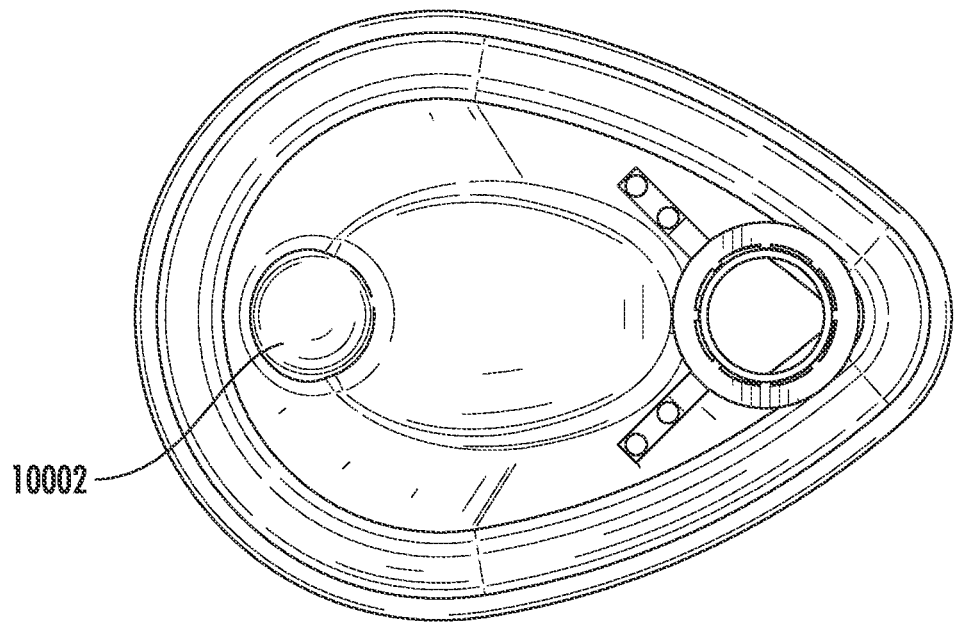
FIGS. 12A and 12B are schematic illustrations of a mask with a bubble which can aid in placement of the fingers of the hand gripping the mask and chin.
Figure 12B:
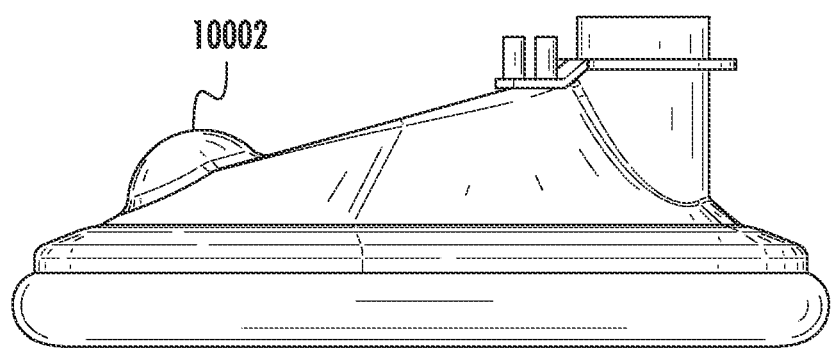
Figure 13A:
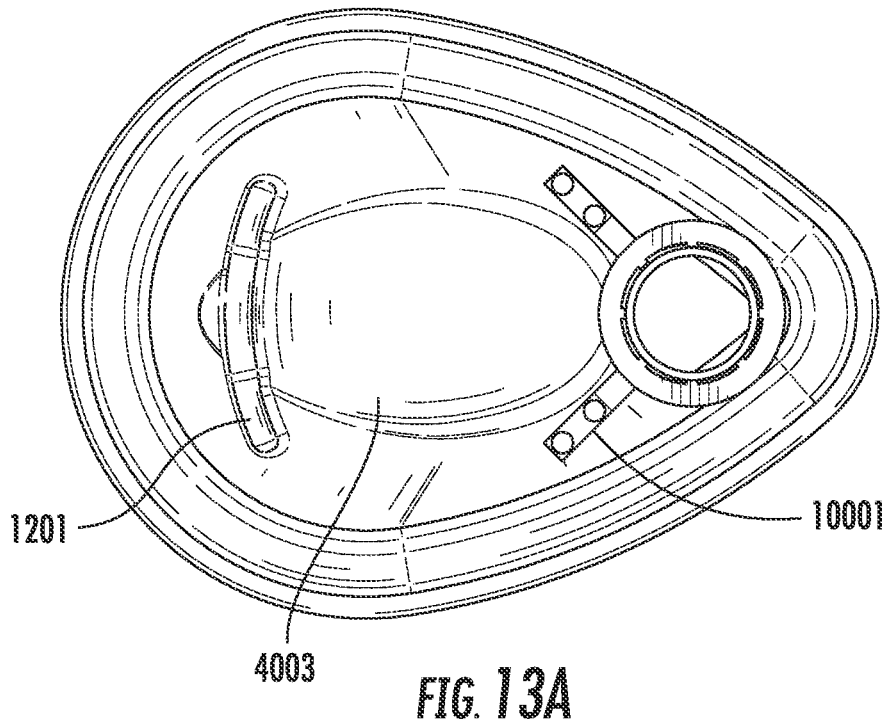
FIGS. 13A-H are schematic illustrations of a convex contoured region mask having one or more ribs.
Figure 13B:
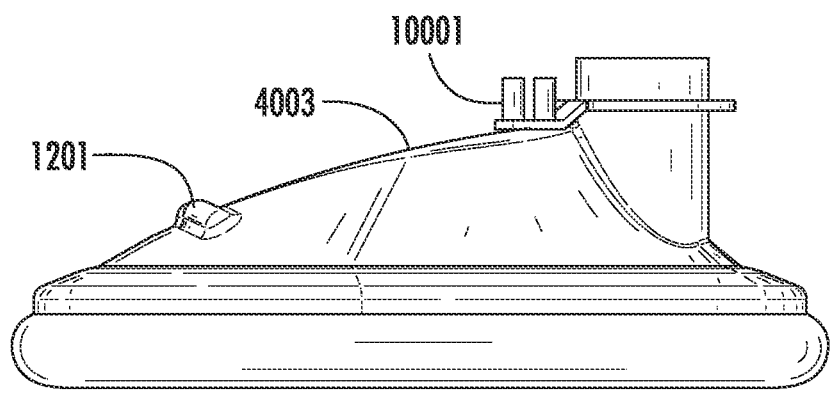
Figure 13C:
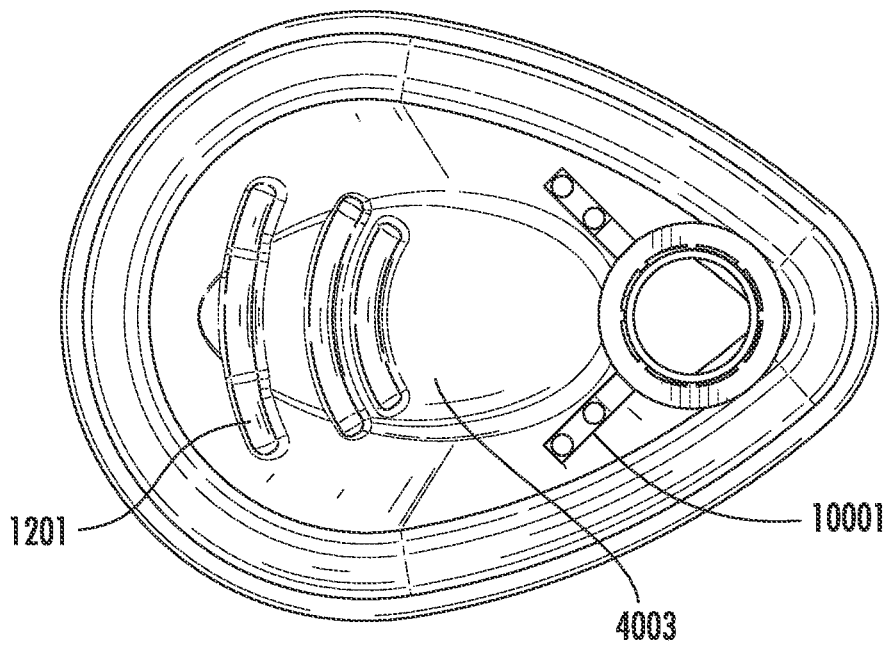
Figure 13D:
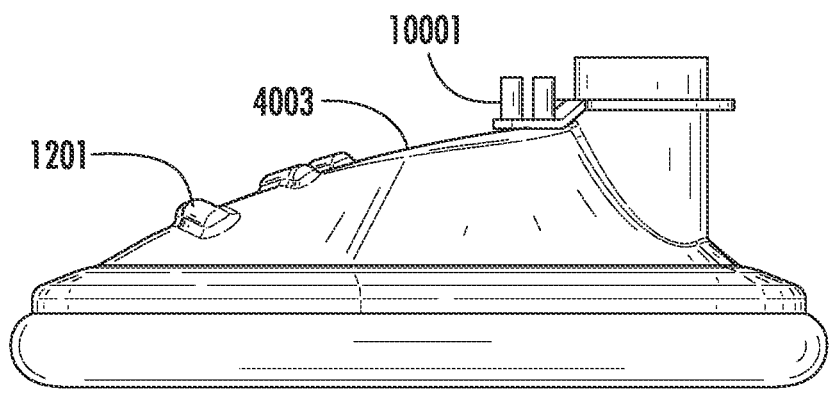
Figure 13E:
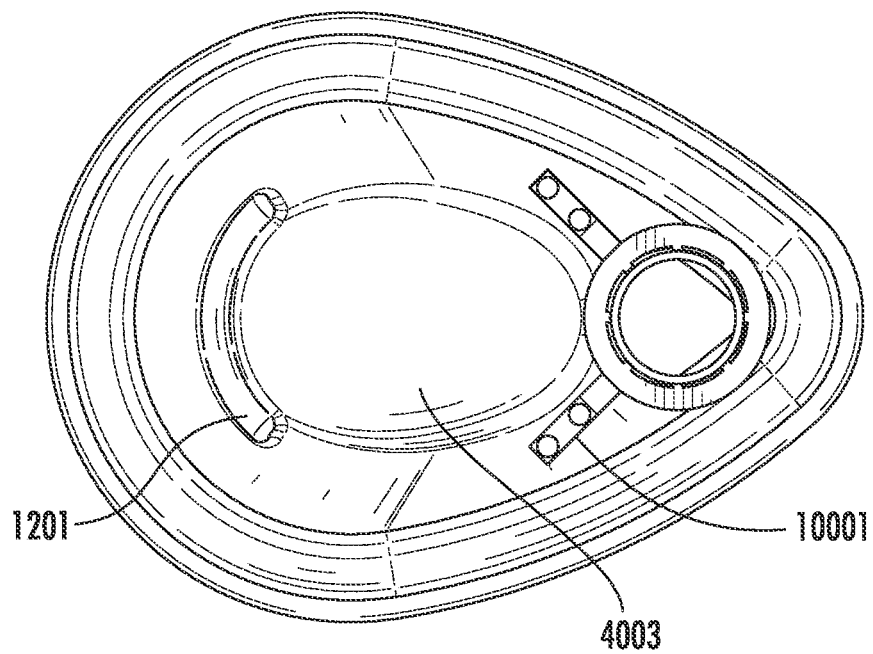
Figure 13F:
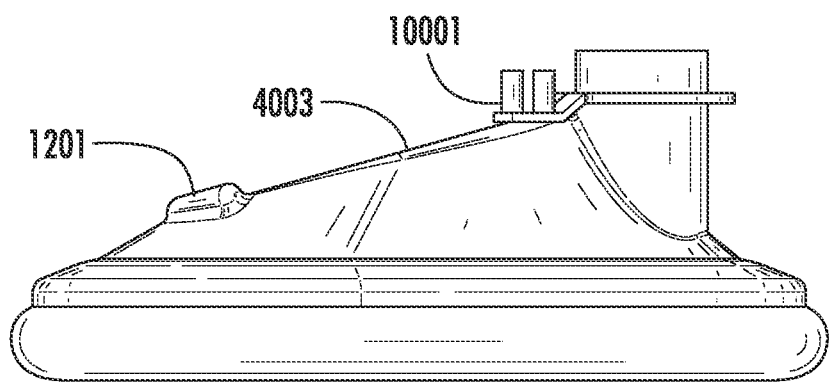
Figure 13G:
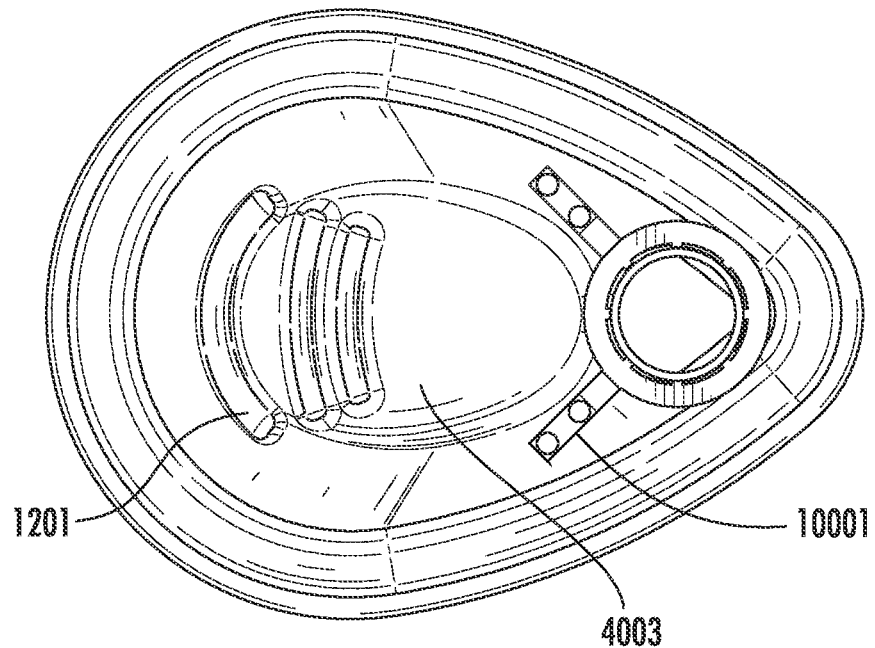
Figure 13H:
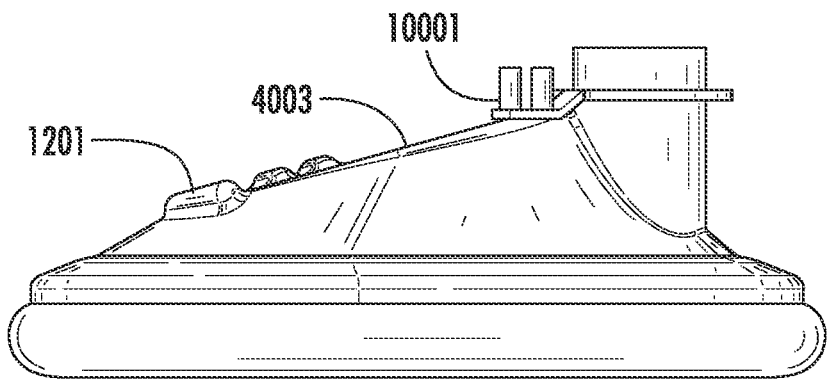

FIGS. 12A and 12B are schematic illustrations of a mask with a bubble 10002 which can aid in placement of the fingers of the hand gripping the mask and chin.

FIGS. 13A-H show embodiments of the mask having one or more ridges 1201 arising out of the contoured region 4003 of the mask.

Figure 14:
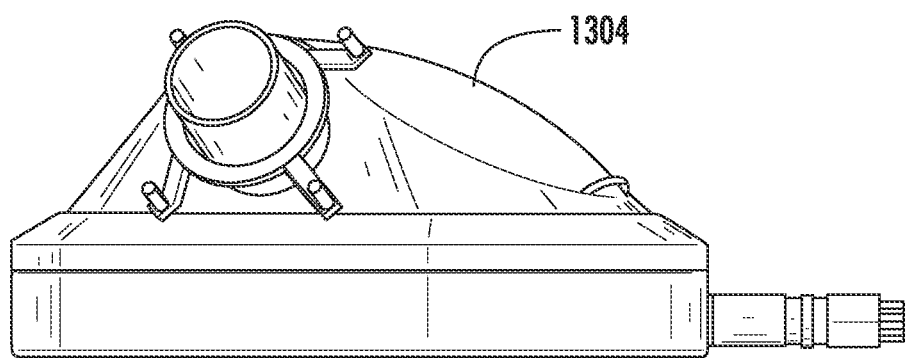
FIG. 14 is a schematic illustration of a mask having a convex contoured region.

FIG. 14 shows an embodiment of the mask where the contoured region 1204 is in a convex rather than a concave configuration. This configuration of the mask can be utilized, for example, if the mask is small, such as a mask made for pediatrics, where the concave nature may not provide enough room for either the pediatrics nose and lips or where the region has become non-optimal when concave to fit the palm of the clinician. As the masks become smaller they become smaller relative to the clinician's hand. As the masks get smaller, the body of the mask optionally moves from concave to convex. By gradually changing the body from concave to convex moving to smaller masks, the described grip is maintained for a wide range of mask sizes. For example, on a small baby, the distance between the center of the mask (where palm pressure is applied) and the chin (where finger tips lift chin) is very short. By making the mask convex it facilitates applying the described grip while allowing a more natural hand position with the fingers flexed less acutely.

The disclosed face masks can be used for ventilation and may eliminate or reduce the awkward pressure on the digits that exists while using existing face masks. The design of the disclosed face masks allow the user to hold the mask firmly and uniformly against the face by applying downward pressure with the palm, while lifting up on the jaw with four fingers, instead of the necessitated claw-like grip now used with existing face masks.

When ventilating, the attending physician or emergency medical technician typically uses a bag-mask device and holds the face mask over a patient's mouth and nose with the left hand and squeezes the bag (develops positive pressure air flow) with the right hand. Problems with this grip technique are well known and documented. Positive pressure mask ventilation is not always successful. The quality of the seal between the mask and the face can be affected by the patient's facial bone structure, facial hair or other factors.

Ventilation with a bag-mask is a complex technique that requires considerable skill and practice. It is even more difficult when attempting to provide ventilation using one hand. Currently, to achieve a good face mask seal requires applying two simultaneous forces in opposite directions with one hand. In order to generate a sufficient grip in this position, the fingers are forced to assume a "claw-like" posture, so that the fingers split around the neck where oxygen flows from the bag to the patient. This is necessary because the oxygen neck is placed symmetrically and distally from the ventilator. It is well documented in the literature that maintaining this grip is uncomfortable, tiring, and painful especially when increased force is necessary to obtain and maintain a seal. Placement of the face mask can be strenuous, painful, and ineffective.

Thus, provided are methods of ventilating a patient. The methods include covering the nose and mouth of the patient with a face mask. At least a portion of the palm of an operator's hand is placed onto the face mask. Each finger of the operator's hand, other than the thumb, is placed under the chin of the patient and using one or more of the fingers to pull the chin towards the mask and palm. Ventilating gas is then supplied to the subject through the mask. Optionally, the operator's left hand is used in each placing step. Optionally, the neck is positioned in the V-shaped position between a forefinger and thumb of the operator. Optionally, the neck is located in the V-shape when the mask is used in applications where the mask is of a size that allows the user to drape the fingers over the back end of the chin while locating the neck between a forefinger and thumb. Such applications optionally involve small sized masks. Optionally, the neck is positioned in the V-shaped are for ventilation of pediatric patients using pediatric sized ventilation masks.

The disclosed designs provide an easier and more reliable seal, as well as ergonomic benefits. The devices would have much the same form factor as a conventional face mask, making them compatible with all existing ventilation systems and also making them compatible with existing mass-production processes. In the disclosed face masks placement of the airway passage is well off center, not symmetrical, and allows the user to apply a completely different technique to place the mask, holding an effective seal.

A number of embodiments of the invention have been described. Nevertheless, it will be understood that various modifications may be made without departing from the spirit and scope of the invention. Accordingly, other embodiments are within the scope of the following claims.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a method is disclosed and discussed each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

What is claimed is:

1. A ventilation mask, comprising:
a. a non-planar body sized to cover the nose and mouth of a patient, the ventilation mask having a mid-sagittal plane, a mid-frontal plane, and a peripheral patient contacting portion, wherein the mid-frontal plane divides the mask into a front portion and a rear portion, wherein the front portion is configured for being positioned closer than the rear portion to a top of a head of the patient;
b. a neck that defines a passage through the body, the passage having a central mid-line axis, and where the central mid-line axis intersects the top surface of the mask at a mid-line intersection point;
c. wherein the top surface of the mask has a center point defined by the intersection of the top surface of the mask, the mid-sagittal plane, and the mid-frontal plane;
d. wherein the mid-line intersection point is offset from the center point and located in the front portion of the mask, and the center point is not encompassed by the passage defined by the neck or any other port or opening; and
e. wherein the top surface of the mask includes a contoured region that is at least partially concave, and the contoured region encompasses the center point of the top surface of the mask, wherein the contoured region is configured to accept at least a portion of the palm extending from the base of the thumb of an operator of the device within the concavity of the contoured region.

2. The ventilation mask of claim 1, wherein the mid-line intersection point is offset from the center point of the top surface of the face mask to an extent that allows placement of at least a portion of an operator's palm between the neck and the mid-sagittal plane of the face mask.

3. The ventilation mask of claim 1, wherein the concavity is configured to accept at least a portion of the left palm of the operator.

4. The ventilation mask of claim 1, wherein the ventilation mask is sized for ventilation of a pediatric patient.

5. The ventilation mask of claim 1, wherein the peripheral patient contacting portion comprises a sealing member.

6. The ventilation mask of claim 5, wherein the sealing member comprises a deformable gas-filled bladder.

7. The ventilation mask of claim 1, wherein the mid-line intersection point is located along the mid-sagittal plane.

8. The ventilation mask of claim 7, wherein the mid-line intersection point is located at a point along the mid-sagittal plane and that is spaced from the center point by a distance at least equal to the radius of the passage.

9. The ventilation mask of claim 8, wherein the mid-line intersection point is located at a point along the mid-sagittal plane and is spaced from the center point by a distance of between 1 and 5 radii of the passage.

10. A ventilation mask, comprising:
a. a non-planar body sized to cover the nose and mouth of a patient, the ventilation mask having a mid-sagittal plane, a mid-frontal plane, a peripheral patient contacting portion and a center region, wherein the mid-frontal plane divides the mask into a front portion and a rear portion, wherein the front portion is configured for being positioned closer than the rear portion to a top of a head of the patient;
b. a neck that defines a passage through the body, the passage having a central mid-line axis that is offset from the center region of the mask and located in the front portion of the mask, and no part of the center region is encompassed by the passage defined by the neck or any other port or opening;
c. wherein the top surface of the mask has a center point defined by the intersection of the top surface of the mask, the mid-sagittal plane, and the mid-frontal plane; and
d. wherein the top surface of the mask includes a contoured region that is at least partially concave, and the contoured region encompasses the center point of the top surface of the mask, wherein the contoured region is configured to accept at least a portion of the palm extending from the base of the thumb of an operator of the device within the concavity of the contoured region.

11. The mask of claim 10, wherein the center region is defined by a radius of 10% of the width of the mask from the left to the right in the mid-sagittal plane of the mask.

* * * * *